US007993832B2

(12) United States Patent
Rosenberg et al.

(10) Patent No.: US 7,993,832 B2
(45) Date of Patent: Aug. 9, 2011

(54) METHODS AND COMPOSITIONS FOR DIAGNOSING AND MONITORING THE STATUS OF TRANSPLANT REJECTION AND IMMUNE DISORDERS

(75) Inventors: Steven Rosenberg, Oakland, CA (US); Kirk Fry, Palo Alto, CA (US); Bin Wu, San Jose, CA (US); Russell L. Dedrick, Kensington, CA (US)

(73) Assignee: XDx, Inc., Brisbane, CA (US)

( * ) Notice: Subject to any disclaimer, the term of this patent is extended or adjusted under 35 U.S.C. 154(b) by 0 days.

(21) Appl. No.: 11/893,236

(22) Filed: Aug. 14, 2007

(65) Prior Publication Data
US 2008/0038746 A1 Feb. 14, 2008

Related U.S. Application Data

(60) Provisional application No. 60/837,698, filed on Aug. 14, 2006.

(51) Int. Cl.
*C12Q 1/68* (2006.01)
*G01N 33/53* (2006.01)

(52) U.S. Cl. ............................................. 435/6; 435/7.1
(58) Field of Classification Search ................... 435/7.1, 435/6
See application file for complete search history.

(56) References Cited

U.S. PATENT DOCUMENTS

| 4,190,535 | A | 2/1980 | Luderer et al. |
| 4,215,051 | A | 7/1980 | Schroeder et al. |
| 4,350,593 | A | 9/1982 | Kessler |
| 4,358,535 | A | 11/1982 | Falkow et al. |
| 4,376,110 | A | 3/1983 | David |
| 4,582,789 | A | 4/1986 | Sheldon, III et al. |
| 4,683,195 | A | 7/1987 | Mullis et al. |
| 4,683,202 | A | 7/1987 | Mullis |
| 4,751,001 | A | 6/1988 | Saunders |
| 4,762,780 | A | 8/1988 | Spector et al. |
| 4,789,630 | A | 12/1988 | Bloch et al. |
| 4,800,159 | A | 1/1989 | Mullis et al. |
| 4,818,418 | A | 4/1989 | Saunders |
| 4,843,155 | A | 6/1989 | Chomczynski |
| 4,889,818 | A | 12/1989 | Gelfand et al. |
| 4,908,318 | A | 3/1990 | Lerner |
| 4,946,778 | A | 8/1990 | Ladner |
| 4,946,952 | A | 8/1990 | Kiefer |
| 4,965,188 | A | 10/1990 | Mullis et al. |
| 5,053,134 | A | 10/1991 | Luderer et al. |
| 5,063,162 | A | 11/1991 | Kiefer |
| 5,066,584 | A | 11/1991 | Gyllensten et al. |
| 5,075,216 | A | 12/1991 | Innis et al. |
| 5,079,352 | A | 1/1992 | Gelfand et al. |
| 5,091,310 | A | 2/1992 | Innis |
| 5,120,525 | A | 6/1992 | Goldenberg |
| 5,142,033 | A | 8/1992 | Innis |
| 5,143,854 | A | 9/1992 | Pirrung et al. |
| 5,210,015 | A | 5/1993 | Gelfand et al. |
| 5,212,071 | A | 5/1993 | Fearon et al. |
| 5,215,882 | A | 6/1993 | Bahl et al. |
| 5,219,727 | A | 6/1993 | Wang et al. |
| 5,264,351 | A | 11/1993 | Harley |
| 5,278,043 | A | 1/1994 | Bannwarth et al. |
| 5,310,652 | A | 5/1994 | Gelfand et al. |
| 5,314,809 | A | 5/1994 | Erlich et al. |
| 5,322,770 | A | 6/1994 | Gelfand |
| 5,340,720 | A | 8/1994 | Stetler |
| 5,346,994 | A | 9/1994 | Chomczynski |
| 5,352,600 | A | 10/1994 | Gelfand et al. |
| 5,374,553 | A | 12/1994 | Gelfand et al. |
| 5,385,824 | A | 1/1995 | Hoet et al. |
| 5,389,512 | A | 2/1995 | Sninsky et al. |
| 5,393,672 | A | 2/1995 | Van Ness et al. |
| 5,405,774 | A | 4/1995 | Abramson et al. |
| 5,407,800 | A | 4/1995 | Gelfand et al. |
| 5,411,876 | A | 5/1995 | Bloch et al. |
| 5,418,149 | A | 5/1995 | Gelfand et al. |
| 5,420,029 | A | 5/1995 | Gelfand et al. |
| 5,426,039 | A | 6/1995 | Wallace et al. |
| 5,445,940 | A | 8/1995 | Brenner et al. |
| 5,455,170 | A | 10/1995 | Abramson et al. |
| 5,459,037 | A | 10/1995 | Sutcliffe et al. |
| 5,466,591 | A | 11/1995 | Abramson et al. |
| 5,468,613 | A | 11/1995 | Erlich et al. |
| 5,476,774 | A | 12/1995 | Wang et al. |
| 5,487,970 | A | 1/1996 | Rowley et al. |
| 5,487,972 | A | 1/1996 | Gelfand et al. |
| 5,491,063 | A | 2/1996 | Fisher et al. |

(Continued)

FOREIGN PATENT DOCUMENTS
EP 0217992 A2 4/1987

(Continued)

OTHER PUBLICATIONS

Abdallah, A. N. et al. (1997). "Evaluation of Plasma Levels of Tumor Necrosis Factor Alpha and Interleukin-6 as Rejection Markers in a Cohort of 142 Heart-Grafted Patients Followed by Endomyocardial Biopsy," *European Heart Journal* 18:1024-1029.
Ahern, H. (Jul. 24, 1995). "Biochemical, Reagent Kits Offer Scientists Good Return on Investment," *The Scientist* 9(15):20-24.
Ajjan, R. A. et al. (1996). "Intrathyroidal Cytokine Gene Expression in Hashimoto's Thyroiditis," *Clinical and Experimental Immunology* 105:523-528.
Akalin, E. et al. (Sep. 2001). "Gene Expression Analysis in Human Renal Allograft Biopsy Samples Using High-Density Oligoarray Technology," *Transplantation* 72(5):948-953.
Alizadeh, A. A. et al. (2000). "Genomic-Scale Gene Expression Profiling of Normal and Malignant Immune Cells," *Current Opinion in Immunology* 12:219-225.

(Continued)

*Primary Examiner* — Kenneth R. Horlick
*Assistant Examiner* — Joyce Tung
(74) *Attorney, Agent, or Firm* — Morrison & Foerster LLP

(57) ABSTRACT

The invention presents methods of using splice variants and reagents thereof for diagnosing and monitoring the status of transplants and immune disorders including diagnosing, monitoring and predicting transplant rejection or non-rejection, steroid responsiveness, and onset or flare of immune disorders.

4 Claims, No Drawings

U.S. PATENT DOCUMENTS

| | | |
|---|---|---|
| 5,491,086 A | 2/1996 | Gelfand et al. |
| 5,501,963 A | 3/1996 | Burckhardt et al. |
| 5,506,145 A | 4/1996 | Bull et al. |
| 5,512,462 A | 4/1996 | Cheng |
| 5,514,556 A | 5/1996 | Shearer et al. |
| 5,538,848 A | 7/1996 | Livak et al. |
| 5,561,058 A | 10/1996 | Gelfand et al. |
| 5,565,339 A | 10/1996 | Bloch et al. |
| 5,569,583 A | 10/1996 | Greenberg et al. |
| 5,571,673 A | 11/1996 | Picone |
| 5,573,906 A | 11/1996 | Bannwarth et al. |
| 5,604,099 A | 2/1997 | Erlich et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,635,365 A | 6/1997 | Ansari et al. |
| 5,641,864 A | 6/1997 | Gelfand |
| 5,658,744 A | 8/1997 | Ochoa et al. |
| 5,665,551 A | 9/1997 | Gelfand et al. |
| 5,674,738 A | 10/1997 | Abramson et al. |
| 5,677,152 A | 10/1997 | Birch et al. |
| 5,693,517 A | 12/1997 | Gelfand et al. |
| 5,707,807 A | 1/1998 | Kato |
| 5,716,787 A | 2/1998 | Dunn et al. |
| 5,721,351 A | 2/1998 | Levinson |
| 5,728,822 A | 3/1998 | Macfarlane |
| 5,766,585 A | 6/1998 | Evans et al. |
| 5,773,258 A | 6/1998 | Birch et al. |
| 5,789,224 A | 8/1998 | Gelfand et al. |
| 5,795,762 A | 8/1998 | Abramson et al. |
| 5,804,375 A | 9/1998 | Gelfand et al. |
| 5,807,522 A | 9/1998 | Brown et al. |
| 5,811,284 A | 9/1998 | Chang et al. |
| 5,837,832 A | 11/1998 | Chee et al. |
| 5,939,270 A | 8/1999 | Haunso et al. |
| 5,939,292 A | 8/1999 | Gelfand et al. |
| 5,958,342 A | 9/1999 | Gamble et al. |
| 5,958,688 A | 9/1999 | Eberwine et al. |
| 5,965,366 A | 10/1999 | Ochoa et al. |
| 5,968,799 A | 10/1999 | Gelfand et al. |
| 5,973,137 A | 10/1999 | Heath |
| 5,981,481 A | 11/1999 | Fearon et al. |
| 5,994,056 A | 11/1999 | Higuchi |
| 5,994,076 A | 11/1999 | Chenchik et al. |
| 6,001,611 A | 12/1999 | Will |
| 6,004,755 A | 12/1999 | Wang |
| 6,010,853 A | 1/2000 | Kanteti et al. |
| 6,020,186 A | 2/2000 | Henco et al. |
| 6,033,860 A | 3/2000 | Lockhart et al. |
| 6,040,138 A | 3/2000 | Lockhart et al. |
| 6,040,166 A | 3/2000 | Erlich et al. |
| 6,045,996 A | 4/2000 | Cronin et al. |
| 6,048,695 A | 4/2000 | Bradley et al. |
| 6,048,709 A | 4/2000 | Falb |
| 6,060,240 A | 5/2000 | Kamb et al. |
| 6,066,322 A | 5/2000 | Levinson |
| 6,066,498 A | 5/2000 | Levinson |
| 6,084,083 A | 7/2000 | Levinson |
| 6,087,112 A | 7/2000 | Dale |
| 6,087,477 A | 7/2000 | Falb et al. |
| 6,090,556 A | 7/2000 | Kato et al. |
| 6,099,823 A | 8/2000 | Falb |
| 6,124,433 A | 9/2000 | Falb et al. |
| 6,127,155 A | 10/2000 | Gelfand et al. |
| 6,132,997 A | 10/2000 | Shannon |
| 6,146,828 A | 11/2000 | Lapidus et al. |
| 6,150,121 A | 11/2000 | Hamawy et al. |
| 6,156,887 A | 12/2000 | Levinson |
| 6,162,604 A | 12/2000 | Jacob |
| 6,168,933 B1 | 1/2001 | Kaser et al. |
| 6,171,785 B1 | 1/2001 | Higuchi |
| 6,177,254 B1 | 1/2001 | Rattner et al. |
| 6,187,534 B1 | 2/2001 | Strom et al. |
| 6,190,857 B1 | 2/2001 | Ralph et al. |
| 6,190,872 B1 | 2/2001 | Slotman |
| 6,194,158 B1 | 2/2001 | Kroes et al. |
| 6,197,563 B1 | 3/2001 | Erlich et al. |
| 6,203,987 B1 | 3/2001 | Friend et al. |
| 6,204,371 B1 | 3/2001 | Levinson |
| 6,214,979 B1 | 4/2001 | Gelfand et al. |
| 6,218,122 B1 | 4/2001 | Friend et al. |
| 6,222,093 B1 | 4/2001 | Marton et al. |
| 6,225,084 B1 | 5/2001 | Falb et al. |
| 6,225,093 B1 | 5/2001 | Grant et al. |
| 6,228,628 B1 | 5/2001 | Gelfand et al. |
| 6,242,185 B1 | 6/2001 | Kaser et al. |
| 6,245,334 B1 | 6/2001 | Seilhammer et al. |
| 6,245,526 B1 | 6/2001 | Yue et al. |
| 6,245,527 B1 | 6/2001 | Busfield et al. |
| 6,248,527 B1 | 6/2001 | Chen et al. |
| 6,248,528 B1 | 6/2001 | Chen et al. |
| 6,251,597 B1 | 6/2001 | Shyjan |
| 6,262,244 B1 | 7/2001 | Houchins et al. |
| 6,274,312 B1 | 8/2001 | Gish et al. |
| 6,280,941 B1 | 8/2001 | Tsao et al. |
| 6,303,321 B1 | 10/2001 | Tracey et al. |
| 6,306,602 B1 | 10/2001 | Sillekens et al. |
| 6,365,352 B1 | 4/2002 | Yerramilli et al. |
| 6,403,304 B1 | 6/2002 | Stashenko et al. |
| 6,410,319 B1 | 6/2002 | Raubitschek et al. |
| 6,797,263 B2 | 9/2004 | Strom et al. |
| 6,811,973 B1 | 11/2004 | Reich |
| 6,900,015 B2 | 5/2005 | Avihingsanon et al. |
| 6,905,827 B2 | 6/2005 | Wohlgemuth et al. |
| 6,964,850 B2 | 11/2005 | Bevilacqua et al. |
| 7,026,121 B1 | 4/2006 | Wohlgemuth et al. |
| 7,118,865 B2 | 10/2006 | Behrens et al. |
| 7,235,358 B2 | 6/2007 | Wohlgemuth et al. |
| 7,514,209 B2 | 4/2009 | Dai et al. |
| 2001/0021700 A1 | 9/2001 | Moore et al. |
| 2002/0042386 A1 | 4/2002 | Rosen et al. |
| 2003/0139466 A1 | 7/2003 | Peritt et al. |
| 2003/0224426 A1 | 12/2003 | Li |
| 2003/0225526 A1 | 12/2003 | Golub et al. |
| 2004/0023246 A1 | 2/2004 | Meuer et al. |
| 2004/0072181 A1 | 4/2004 | Whitehead et al. |
| 2004/0197786 A1 | 10/2004 | Sugita et al. |
| 2005/0186637 A1* | 8/2005 | Yu et al. ........................ 435/7.1 |
| 2005/0281815 A1* | 12/2005 | Eshel et al. ................ 424/144.1 |
| 2006/0051803 A1 | 3/2006 | Wohlgemuth et al. |
| 2006/0088836 A1 | 4/2006 | Wohlgemuth et al. |
| 2006/0216707 A1 | 9/2006 | Stuhlmuller et al. |
| 2006/0263813 A1 | 11/2006 | Rosenberg et al. |
| 2007/0037144 A1 | 2/2007 | Wohlgemuth et al. |
| 2007/0037166 A1 | 2/2007 | Wohlgemuth et al. |
| 2007/0037167 A1 | 2/2007 | Wohlgemuth et al. |
| 2007/0248978 A1 | 10/2007 | Lal et al. |
| 2008/0199853 A1 | 8/2008 | Wohlgemuth et al. |

FOREIGN PATENT DOCUMENTS

| | | |
|---|---|---|
| EP | 0217102 B1 | 1/1992 |
| EP | 1077254 A2 | 2/2001 |
| EP | 1162276 A2 | 12/2001 |
| WO | WO-91/18626 A1 | 12/1991 |
| WO | WO-94/23023 A1 | 10/1994 |
| WO | WO-95/17506 A1 | 6/1995 |
| WO | WO-96/39536 A1 | 12/1996 |
| WO | WO-97/16568 A1 | 5/1997 |
| WO | WO-97/30065 A1 | 8/1997 |
| WO | WO-98/24935 A1 | 6/1998 |
| WO | WO-99/04251 A1 | 1/1999 |
| WO | WO-99/10536 A1 | 3/1999 |
| WO | WO-99/11782 A1 | 3/1999 |
| WO | WO-99/11822 A1 | 3/1999 |
| WO | WO-99/15700 A1 | 4/1999 |
| WO | WO-99/52541 A2 | 10/1999 |
| WO | WO-99/57130 A1 | 11/1999 |
| WO | WO-00/04191 A1 | 1/2000 |
| WO | WO-00/12753 A1 | 3/2000 |
| WO | WO-0023573 A2 | 4/2000 |
| WO | WO-00/29574 | 5/2000 |
| WO | WO-00/46372 A2 | 8/2000 |
| WO | WO-00/52209 A1 | 9/2000 |
| WO | WO-00/55375 A1 | 9/2000 |
| WO | WO-00/58473 A2 | 10/2000 |
| WO | WO-00/63372 A1 | 10/2000 |
| WO | WO-00/73498 A1 | 12/2000 |

| | | |
|---|---|---|
| WO | WO-00/78808 A1 | 12/2000 |
| WO | WO-01/14557 A1 | 3/2001 |
| WO | WO-01/20004 A2 | 3/2001 |
| WO | WO-01/23426 A2 | 4/2001 |
| WO | WO-01/23564 A1 | 4/2001 |
| WO | WO-01/25473 A1 | 4/2001 |
| WO | WO-01/29269 A2 | 4/2001 |
| WO | WO-01/32927 A2 | 5/2001 |
| WO | WO-01/40302 A2 | 6/2001 |
| WO | WO-01/47944 A2 | 7/2001 |
| WO | WO-01/54733 A1 | 8/2001 |
| WO | WO-01/55164 A1 | 8/2001 |
| WO | WO-01/55201 A1 | 8/2001 |
| WO | WO-01/55203 A1 | 8/2001 |
| WO | WO-01/55205 A1 | 8/2001 |
| WO | WO-01/55328 A2 | 8/2001 |
| WO | WO-01/55368 A1 | 8/2001 |
| WO | WO-01/57182 A2 | 8/2001 |
| WO | WO-01/60860 A2 | 8/2001 |
| WO | WO-01/71005 A2 | 9/2001 |
| WO | WO-01/81916 A2 | 11/2001 |
| WO | WO-01/86003 A2 | 11/2001 |
| WO | WO-02/00677 A1 | 1/2002 |
| WO | WO-02/00928 A2 | 1/2002 |
| WO | WO-02/28999 A2 | 4/2002 |
| WO | WO-02/057414 A2 | 7/2002 |
| WO | WO-03/072035 A2 | 9/2003 |
| WO | WO-03/090694 A2 | 11/2003 |
| WO | WO-2004/042346 A2 | 5/2004 |
| WO | WO-2004/074815 A | 9/2004 |
| WO | WO-2004/108899 A2 | 12/2004 |
| WO | 2006/122295 A2 | 11/2006 |

OTHER PUBLICATIONS

Alizadeh, A. A. et al. (Feb. 2000). "Distinct Types of Diffuse Large B-cell Lymphoma Identified by Gene Expression Profiling," *Nature* 403:503-511.

Alizadeh, A. et al. (1998). "Probing Lymphocyte Biology by Genomic-Scale Gene Expression Analysis," *Journal of Clinical Immunology* 18(6):373-379.

Alizadeh, A. et al. (1999). "The Lymphochip: A Specialized cDNA Microarray for the Genomic-scale Analysis of Gene Expression in Normal and Malignant Lymphocytes," *Cold Spring Harbor Symposia on Quantitative Biology* 54:71-78.

Alpert, S. et al. (Dec. 1995). "The Relationship of Granzyme A and Perforin Expression to Cardiac Allograft Rejection and Dysfunction," *Transplantation* 60(12):1478-1485.

Amaro, A. et al. (1995). "Plasma Leukocyte Elastase Concentration in Angiographically Diagnosed Coronary Artery Disease," *European Heart Journal* 16:615-622.

Arnett, F. C. et al. (Mar. 1988). "The American Rheumatism Association 1987 Revised Criteria for the Classification of Rheumatoid Arthritis," *Arthritis and Rheumatism* 31(3):315-324.

Aukrust, P. et al. (1999). "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes," *Circulation* 100:614-620.

Australian Written Opinion and Search Report mailed Oct. 7, 2005, for Singapore Application No. SG 200406287-3 filed Apr. 24, 2003, 12 pages.

Autieri, M. V. et al. (2002). "Allograft Inflammatory Factor-1 Expression Correlates with Cardiac Rejection and Development of Cardiac Allograft Vasculopathy," *Circulation* 106:2218-2223.

Baechler, E. C. et al. (Mar. 2003). "Interferon-Inducible Gene Expression Signature in Peripheral Blood Cells of Patients with Severe Lupus," *Proceedings of the National Academy of Sciences* 100(5):2610-2615.

Bakke, A. C. et al. (2001). "Neutrophil CD64 Expression Distinguishing Acute Inflammatory Autoimmune Disease from Systemic Infections," *Clinical and Applied Immunology Reviews* 1:267-275.

Bass, C. A. (Oct. 1993). "Clinical Evaluation of a New Polymerase Chain Reaction Assay for Detection of *Chlamydia trachomatis* in Endocervical Specimens," *Journal of Clinical Microbiology* 31(10):2648-2653.

Bave, U. (2000). "The Combination of Apoptotic U937 Cells and Lupus IgG is a Potent IFN-Alpha Inducer," *The Journal of Immunology* 165:3519-3526.

Bave, U. (2001). "Activation of Natural Interferon-Alpha Producing Cells by Apoptotic U937 Cells Combined with Lupus IgG and its Regulation by Cytokines," *Journal of Autoimmunity* 17:71-80.

Belch, J. J. F. et al. (Apr. 1997). "The White Blood Cell Adhesion Molecule E-Selectin Predicts Restenosis in Patients With Intermittent Claudication Undergoing Percutaneous Transluminal Angioplasty," *Circulation* 95(8):2027-2031.

Bertone, P. et al. (Dec. 24, 2004). "Global Identification of Human Transcribed Sequences with Genome Tiling Arrays," *Science* 306:2242-2246.

Bittner, M. et al. (Aug. 2000). "Molecular Classification of Cutaneous Malignant Melanoma by Gene Expression Profiling," *Nature* 406:536-540.

Boelaert, M. et al. (May 1999). "Latent Class Analysis Permits Unbiased Estimates of the Validity of DAT for the Diagnosis of Visceral Leishmaniasis," *Tropical Medicine & International Health* 4(5):395-401.

Bombardier, C. et al. (Jun. 1992), "Derivation of the SLEDAI—A Disease Activity Index for Lupus Patients," *Arthritis and Rheumatism* 35(6):630-640.

Bustin, S. A. (2000). "Absolute Quantification of mRNA Using Real-Time Reverse Transcription Polymerase Chain Reaction Assays," *Journal of Molecular Endocrinology* 25:169-193.

Chang, D. M. et al. (1996). "Cytokines and Cell Surface Markers in Prediction of Cardiac Allograft Rejection," *Immunological Investigations* 25(1&2):13-21.

Chebath, J. et al. (Mar. 1987). "Four Different Forms of Interferon-Induced 2', 5'-Oligo(A) Synthetase Identified by Immunoblotting in Human Cells," *The Journal of Biological Chemistry* 262(8):3852-2857.

Chen, J. et al. (Aug. 1996). "Identification of Differentially Expressed Genes in Rat Aortic Allograft Vasculopathy," *American Journal of Pathology* 149(2):597-611.

Cheung, V. et al. (Mar. 2003). "Natural Variation in Human Gene Expression Assessed in Lymphoblastoid Cells," *Nature Genetics* 33:422-425.

Creemers, P. et al. (2002). "Evaluation of Peripheral Blood CD4 and CD8 Lymphocyte Subsets, CD69 Expression and Histologic Rejection Grade as Diagnostic Markers for the Presence of Cardiac Allograft Rejection," *Transplant Immunology* 10:285-292.

Damas, J. K. et al. (2001). "Enhanced Gene Expression of Chemokines and their Corresponding Receptors in Mononuclear Blood Cells in Chronic Heart Failure—Modulatory Effect of Intravenous Immunoglobin," *Journal of the American College of Cardiology* 38(1):187-193.

Davas, E. M. et al. (1999). "Serum IL-6, TNF-alpha, p55 srTNF-alpha, p75srTNF-alpha, srIL-2-alpha Levels and Disease Activity in Systemic Lupus Erythematosus," *Clinical Rheumatology* 18:17-22.

Deng, M. C. et al. (Nov. 1995). "The Relation of Interleukin-6, Tumor Necrosis Factor-Alpha, IL-2, and IL-2 Receptor Levels to Cellular Rejection, Allograft Dysfunction, and Clinical Events Early After Cardiac Transplantation," *Transplantation* 60(10):1118-1124.

Deuel, T. F. et al. (Jul. 1981). "Platelet Factor 4 is Chemotactic for Neutrophils and Monocytes," *Proceedings of the National Academy of Sciences* 78(7):4584-4587.

Deuel, T. F. et al. (Jun. 1977). "Amino Acid Sequence of Human Platelet Factor 4," *Proceedings of the National Academy of Sciences* 74(6):2256-2258.

Dietz, A. B. et al. (2000). "Maturation of Human Monocyte-Derived Dendritic Cells Studied by Microarray Hybridization," *Biochemical and Biophysical Research Communications* 275:731-738.

Doi, S. et al. (1994). "Polymerase Chain Reaction Quantification of Cytokine Messenger RNA Expression in Peripheral Blood Monocluear Cells of Patients with Acute Exacerbations of Asthma: Effect of Glucocorticoid Therapy," *Clinical and Experimental Allergy* 24:854-867.

Dudek, A. Z. et al. (Jun. 2003). "Platelet Factor 4 Promotes Adhesion of Hematopoietic Progenitor Cells and Binds IL-8: Novel Mechanisms for Modulation of Hematopoiesis," *Blood* 101(12):4687-4694.

Dugre, F. J. (Oct. 2000). "Cytokine and Cytotoxic Molecule Gene Expression Determined in Peripheral Blood Mononuclear Cells in the Diagnosis of Acute Renal Rejection," *Transplantation* 70(7):1074-1080.

Edman, C. F. et al. (1997). "Electric Field Directed Nucleic Acid Hybridization on Microchips," *Nucleic Acids Research* 25(24):4907-4914.

Eisen, M. B. et al. (Dec. 1998). "Cluster Analysis and Display of Genome-Wide Expression Patterns," *Proceedings of the National Academy of Sciences* 95:14863-14868.

EMBL-EBI Accession No. AA053887, last updated Aug. 31, 2006, located at <http://www.ebi.ac.uk/cgi-bin/dbfetch?db=embl&id=AA053887&style=raw> visited on Oct. 31, 2007. (3 pages).

EMBL-EBI Accession No. AAC77576, located at <http://www.ebi.ac.uk/cgi-bin/dbfetch?db=emblcds&id=AAC77576&style=raw> visited on Oct. 31, 2007. (1 page).

EMBL-EBI Accession No. AAK80490, located at <http://www.ebi.ac.uk/cgi-bin/dbfetch?db=emblcds&id=AAK80490&style=raw> visited on Oct. 31, 2007. (1 page).

EMBL-EBI Accession No. AI775145, last updated Jun. 21, 2002, located at <http://www.ebi.ac.uk/cgi-bin/dbfetch?db=embl&id=AI755145&style=raw> visited on Oct. 31, 2007. (2 pages).

EMBL-EBI Accession No. AK000354, last updated Sep. 12, 2006, located at <http://www.ebi.ac.uk/cgi-bin/dbfetch?db=embl&id=AK000354&style=raw> visited on Oct. 31, 2007. (3 pages).

EMBL-EBI Accession No. AV742425, last updated Oct. 10, 2000, located at <http://www.ebi.ac.uk/cgi-bin/dbfetch?db=embl&id=AV742425&style=raw> visited on Oct. 31, 2007. (2 pages).

EMBL-EBI Accession No. AW969353, last updated Jun. 8, 2000, located at <http://www.ebi.ac.uk/cgi-bin/dbfetch?db=embl&id=AW969353&style=raw> visited on Oct. 31, 2007. (1 page).

EMBL-EBI Accession No. G06338, last updated Mar. 4, 2000, located at <http://www.ebi.ac.uk/cgi-bin/dbfetch?db=embl&id=G06338&style=raw> visited on Oct. 31, 2007. (2 pages).

EMBL-EBI Accession No. L26474, last updated Jan. 9, 2007, located at <http://www.ebi.ac.uk/cgi-bin/dbfetch?db=embl&id=L26474&style=raw> visited on Oct. 31, 2007. (6 pages).

EMBL-EBI Accession No. M23068, last updated Nov. 14, 2006, located at <http://www.ebi.ac.uk/cgi-bin/dbfetch?db=embl&id=M23068&style=raw> visited on Oct. 31, 2007. (2 pages).

EMBL-EBI Accession No. V00497, last updated Nov. 20, 2004, located at <http://www.ebi.ac.uk/cgi-bin/dbfetch?db=embl&id=V00497&style=raw> visited on Oct. 31, 2007. (5 pages).

Fandrey, J. et al. (Feb. 1, 1993). "In Vivo and in Vitro Regulation of Erythropoietin mRNA: Measurement by Competitive Polymerase Chain Reaction," *Blood* 81(3)1617-623.

Felson, D. T. et al. (Jun. 1995). "American College of Rheumatology. Preliminary Definition of Improvement in Rheumatoid Arthritis," *Arthritis and Rheumatism* 38(6):727-735.

Finger, L. R. et al. (1997). "The Human PD-1 Gene: Complete cDNA, Genomic Organization, and Developmentally Regulated Expression in B Cell Progenitors," *Gene* 197:177-187.

Flechner, S. M. et al. (2004). "Kidney Transplant Rejection and Tissue Injury by Gene Profiling of Biopsies and Peripherals Blood Lymphocytes," *American Journal of Transplantation* 4:1475-1489.

Fu, G. et al. (2002). "Representational Difference Analysis in a Lupus-Prone Mouse Strain Results in the Identification of an Unstable Region of the Genome on Chromosome 11," *Nucleic Acids Research* 30(6):1394-1400.

Fullerton, S. M. et al. (Mar. 1994). "Molecular and Population Genetic Analysis of Allelic Sequence Diversity at the Human Beta-Globin Locus," *Proceedings of the National Academy of Sciences* 91:1805-1809.

Gabay, C. et al. (1997). "Circulating Levels of Tumor Necrosis Factor Soluble Receptors in Systemic Lupus Erythematosus are Significantly Higher than in Other Rheumatic Diseases and Correlate with Disease Activity," *The Journal of Rheumatology* 24(2):303-308.

Galon, J. et al. (Jan. 2002). "Gene Profiling Reveals Unknown Enhancing and Suppressive Actions of Glucocorticoids on Immune Cells," *The FASEB Journal* 16:61-71.

GenBank Accession No. AL591031, located at <http://www.ncbi.nlm.nih.gov/entrez/viewerfcgi?db=nuccore&id=16073692> visited on Jun. 27, 2007. (41 pages).

GenBank Accession No. Y10376, last updated May 14, 1997, located at <http://www.ncbi.nlm.nih.gov/entrez/viewer.fcgi?db=nuccore&id=2052057> visited on Apr. 8, 2008. (3 pages).

Ghosh, A. et al. (Jul. 2001). "A Specific Isozyme of 2'-5' Oligoadenylate Synthetase is a Dual Function Proapoptotic Protein of the Bcl-2 Family," *The Journal of Biological Chemistry* 276(27):25477-25455.

Glynne, R. et al. (2000). "B-Lymphocyte Quiescence, Tolerance and Activation as Viewed by Global Gene Expression Profiling on Microarrays," *Immunological Reviews* 176:216-246.

Glynne, R. J. et al. (2000). "Genomic-Scale Gene Expression Analysis of Lymphocyte Growth, Tolerance and Malignancy," *Current Opinion in Immunology* 12:210-214.

Golden-Mason, L. et al. (2000). "Differential Expression of Lymphoid and Myeloid Markers on Differentiating Hematopoietic Stem Cells in Normal and Tumor-Bearing Adult Human Liver," *Hepatology* 31(6):1251-1256.

Golub, T. R. et al. (Oct. 1999). "Molecular Classification of Cancer: Class Discovery and Class Prediction by Gene Expression Monitoring," *Science* 286:531-537.

Gorczynski, R. M. (1996). "Correlation of Peripheral Blood Lymphocyte and Intragraft Cytokine mRNA Expression with Rejection in Orthotopic Liver Transplantation," *Surgery* 120(3):496-502.

Grant, S. C. D. et al. (Aug. 1996). "Serum Cytokines in Human Heart Transplant Recipients," *Transplantation* 62(4):480-491.

Griffiths, G. M. et al. (1991). "Granzyme A and Perforin as Markers for Rejection in Cardiac Transplantation," *European Journal of Immunology* 21:687-692.

Gullestad, L. et al. (1999). "Effect of High- Versus Low-Dose Angiotensin Converting Enzyme Inhibition on Cytokine Levels in Chronic Heart Failure," *Journal of the American College of Cardiology* 34(7):2061-2067.

Harlow, E. et al. (1988). *Antibodies: A Laboratory Manual.* Cold Spring Harbor Laboratory: New York, NY, 9 pages. (Table of Contents).

Hastie, T. et al. (Aug. 2000). "'Gene Shaving' as a Method for Identifying Distinct Sets of Genes with Similar Expression Patterns," *Genome Biology* 1(2):research0003.1-0003.21.

Hastie, T. et al. (Jan. 2001). "Supervised Harvesting of Expression Trees," *Genome Biology* 2(1): research 0003.1-0003.12.

Hayward, A. L. et al. (1998). "Modeling and Analysis of Competitive RT-PCR," *Nucleic Acids Research* 26(11):2511-2518.

Hayward-Lester, A. et al. (1995). "Accurate and Absolute Quantitative Measurement of Gene Expression by Single Tube RT-PCR and HPLC," *Genome Research* 5:494-499.

Heller, R. A. et al. (Mar. 1997). "Discovery and Analysis of Inflammatory Disease-Related Genes Using cDNA Microarrays," *Proceedings of the National Academy of Sciences* 94:2150-2155.

Hendricks, D. A. et al. (Nov. 1995). "Quantitation of HBV DNA in Human Serum Using a Branched DNA (bDNA) Signal Amplification Assay," *American Journal of Clinical Pathology* 104 (5):537-546.

Higuchi, K. et al. (1998). "Serum 2'-5' Oligoadenylate Synthetase Activity in Children. 2. Serum 2'-5' Oligoadenylate Synthetase in Childhood Collagen Disease," 342625a, *Chemical Abstracts* 129(26):406.

Hooks, J. J. et al. (1979). "Immune Interferon in the Circulation of Patients with Autoimmune Disease," *The New England Journal of Medicine* 301(1):5-8.

Hooks, J. J. et al. (Apr. 1982). "Multiple Interferons in the Circulation of Patients with Systemic Lupus Erythematosus and Vasculitis," *Arthritis and Rheumatism* 25(4):396-400.

Hsieh, H.-G. et al. (2001). "IL-17 Expression as a Possible Predictive Parameter for Subclinical Renal Allograft Rejection," *Transplant International* 14:287-298.

Iida, K. et al. (May 1982). "Complement Receptor (CR1) Deficiency in Erythrocytes from Patients with Systemic Lupus Erythematosus," *The Journal of Experimental Medicine* 155:1427-1438.

International Search Report and Written Opinion mailed Aug. 25, 2008, for PCT Application No. PCT/US07/08909 filed Apr. 9, 2007, 10 pages.

International Search Report and Written Opinion mailed Jun. 25, 2008, for PCT Application No. PCT/US06/18381 filed May 11, 2006, 8 pages.

International Search Report and Written Opinion mailed Mar. 27, 2008, for PCT Application No. PCT/US05/31806 filed Sep. 8, 2005, 14 pages.

International Search Report and Written Opinion mailed Sep. 10, 2008, for PCT Application No. PCT/US07/18135 filed Aug. 14, 2007, 12 pages.

International Search Report mailed Jul. 18, 2002, for PCT Application No. PCT/US01/47856 filed Oct. 22, 2001, 3 pages.

International Search Report mailed Mar. 1, 2001, for PCT Application No. PCT/US00/17846 filed Jun. 28, 2000, 2 pages.

International Search Report mailed Sep. 23, 2005, for PCT Application No. PCT/US03/12946 filed Apr. 24, 2003, 4 pages.

International Search Report mailed Sep. 30, 2004, for PCT Application No. PCT/US03/13015 filed Apr. 24, 2003, 5 pages.

Jagota, A. (2000). "Nearest Neighbor Classifiers" Chapter 11 In *Data Analysis and Classification for Bioinformatics*. Department of Computer Science, University of California, Santa Cruz, pp. 92-93.

Jardi, M. et al. (1994). "Urokinase Receptor (UPAR) Expression During Hematopoietic Maturation," *Journal of Drug Targeting* 8(Suppl 1):51.

Joulin, V. et al. (Oct. 25, 1988). "Isolation and Characterization of the Human 2,3-Bisphosphoglycerate Mutase Gene," *The Journal of Biological Chemistry* 263(30):15785-15790.

Jude, B. et al. (Oct. 1994). "Evidence for Time-Dependent Activation of Monocytes in the Systemic Circulation in Unstable Angina but Not in Acute Myocardial Infarction or in Stable Angina," *Circulation* 90(4):1662-1668.

Kang, J. J. et al. (2000). "Transcript Quantitation in Total Yeast Cellular RNA Using Kinetic PCR," *Nucleic Acids Research* 28(2):e2, 8 pages.

Kasprzycka, M. et al. (2002). "Expression of FasL Gene in T cells of Renal Allograft Recipients," *Immunology Letters* 80:9-13.

Kassirer, M. et al. (Sep. 1999). "Increased Expression of the CD11b/CD18 Antigen on the Surface of Peripheral White Blood Cells in Patients with Ischemic Heart Disease: Further Evidence for Smoldering Inflammation in Patients with Atherosclerosis," *American Heart Journal* 138(3):555-559.

Katz, M. H. (1999). "Assumptions of Multiple Linear Regression, Multiple Logistic Regression, and Proportional Hazards Analysis" In *Multivariable Analysis: A Practical Guide for Clinicians*. Cambridge University Press: Cambridge, United Kingdom, pp. 36-42.

Keembiyehetty, C. et al. (Mar. 2006). "Mouse Glucose Transporter 9 Splice Variants Are Expressed in Adult Liver and Kidney and Are Up-regulated in Diabetes," *Molecular Endocrinology* 20(3):686-697.

Kelsen, S. et al. (2004). "The Chemokine Receptor CXCR3 and its Splice Variant are Expressed in Human Airway Epithelial Cells," *American Journal of Physiology-Lung Cellular and Molecular Physiology* 287: L584-L591.

Kendler, K. S. et al. (Jun. 1998). "The Structure of Psychosis Latent Class Analysis of Probands from the Roscommon Family Study," *Archives of General Psychiatry* 55:492-499.

Khan, J. et al. (Jun. 2001). "Classification and Diagnostic Prediction of Cancers Using Gene Expression Profiling and Artificial Neural Networks," *Nature Medicine* 7(6):673-679.

Kimball, P. et al. (Feb. 1995). "Cytokine Panel Predicts Early Rejection of Therapeutic Response After Cardiac Transplantation," *Transplantation Proceedings* 27(1):1286-1287.

Kobashigawa, J. et al. (Aug. 1998). "A Randomized Active-Controlled Trial of Mycophenolate Mofetil in Heart Transplant Recipients," *Transplantation* 66(4):507-515.

Krause, S. W. (1998). "Carboxypeptidase M as a Marker of Macrophage Maturation," *Immunological Reviews* 161:119-127.

Kumar, R. et al. (Oct. 1994). "Cell Cycle-Dependent Modulation of Alpha-Interferon-Inducible Gene Expression and Activation of Signaling Components in Daudi Cells," *The Journal of Biological Chemistry* 269(41):25437-25441.

Kumar, S. et al. (2000). "Expansion and Molecular Evolution of the Interferon-Induced 2'-5' Oligoadenylate Sythetase Gene Family," *Molecular Biology and Evolution* 17(5):738-750.

Toogood, G. J. et al. (Sep. 1996). "The Immune Response Following Small Bowel Transplantation," *Transplantation* 62(6):851-855.

Toronen, P. et al. (1999). "Analysis of Gene Expression Data Using Self-Organizing Maps," *FEBS Letters* 451:142-146.

Torre-Amione, G. et al. (Apr. 1996). "Proinflammatory Cytokine Levels in Patients with Depressed Left Ventricular Ejection Fraction: A Report from the Studies of Left Ventricular Dysfunction (SOLVD)," *Journal of the American College of Cardiology* 27(5):1201-1206.

Tsutamoto, T. et al. (Mar. 2000). "Angiotensin II Type 1 Receptor Antagonist Decreases Plasma Levels of Tumor Necrosis Factor Alpha, Interleukin-6 and Soluble Adhesion Molecules in Patients with Chronic Heart Failure," *Journal of the American College of Cardiology* 35(3):714-721.

Tusher, V. G. et al. (Apr. 2001). "Significance Analysis of Microarrays Applied to the Ionizing Radiation Response," *Proceedings of the National Academy of Sciences* 98(9):5116-5121.

U.S. Office Action mailed Apr. 1, 2008, for U.S. Appl. No. 10/511,937, filed Jul. 22, 2005, 6 pages.

U.S. Office Action mailed Jul. 18, 2008, for U.S. Appl. No. 10/990,275, filed Nov. 15, 2004, 4 pages.

U.S. Office Action mailed Jun. 15, 2007, for U.S. Appl. No. 11/223,492, filed Sep. 8, 2005, 20 pages.

U.S. Office Action mailed Mar. 5, 2008, for U.S. Appl. No. 11/223,492, filed Sep. 8, 2005, 13 pages.

U.S. Office Action mailed Oct. 3, 2007, for U.S. Appl. No. 10/990,275, filed Nov. 15, 2004, 6 pages.

U.S. Office Action mailed Oct. 5, 2007, for U.S. Appl. No. 10/990,298, filed Nov. 15, 2004, 5 pages.

U.S. Office Action mailed Oct. 8, 2008, for U.S. Appl. No. 10/511,937, filed Jul. 22, 2005, 4 pages.

U.S. Office Action mailed Sep. 19, 2008, for U.S. Appl. No. 10/512,028, filed Jul. 21, 2005, 6 pages.

Umek, R. M. et al. (May 2001). "Electronic Detection of Nucleic Acids: A Versatile Platform for Molecular Diagnostics," *Journal of Molecular Diagnostics* 3(2):74-84.

U.S. Appl. No. 11/938,227, filed Nov. 9, 2007 for Lal et al.

U.S. Appl. No. 12/235,969, filed Sep. 23, 2008 for Wohlgemuth et al.

Vallin, H. et al. (1999). "Anti-Double-Stranded DNA Antibodies and Immunostimulatory Plasmid DNA in Combination Mimic the Endogenous IFN-Alpha Inducer in Systemic Lupus Erythematosus," *The Journal of Immunology* 163:6306-6313.

Vandevyver, C. et al. (1998). "Cytokine mRNA Profile of Myelin Basic Protein Reactive T-Cell Clones in Patients with Multiple Sclerosis," *Autoimmunity* 28:77-89.

Vasconcellos, L. M. et al. (Sep. 1998). "Cytotoxic Lymphocyte Gene Expression in Peripheral Blood Leukocytes Correlates with Rejecting Renal Allografts," *Transplantation* 66(5):562-566.

Vignali, D. A. A. (2000). "Multiplexed Particle-Based Flow Cytometric Assays," *Journal of Immunological Methods* 243:243-255.

Vincenti, F. et al. (May 2001). "Multicenter Trial Exploring Calcineurin Inhibitors Avoidance in Renal Transplantation," *Transplantation* 71(9):1282-1287.

Vu, H. K. (2000). "A Method for Quantification of Absolute Amounts of Nucleic Acids by (RT)-PCR and a New Mathematical Model for Data Analysis," *Nucleic Acids Research* 28(7):e18, 9 pages.

Watanabe-Fukunaga, R. et al. (Mar. 1992). "Lymphoproliferation Disorder in Mice Explained by Defects in Fas Antigen that Mediates Apoptosis," *Nature* 356:314-317.

Weast, R. C. ed. (1968). *Handbook of Chemistry and Physics*. 49th Edition, The Chemical Rubber Co.: Cleveland, Ohio, 2 pages.

Welsh, J. B. et al. (Jan. 2001). "Analysis of Gene Expression Profiles in Normal and Neoplastic Ovarian Tissue Samples Identifies Candidate Molecular Markers of Epithelial Ovarian Cancer," *Proceedings of the National Academy of Sciences* 98(3):1176-1181.

Westin, L. et al. (Feb. 2000). "Anchored Multiplex Amplification on a Microelectronic Chip Array," *Nature Biotechnology* 18:199-204.

Whitehead, J. (Date Unknown). "An Introduction to Logistic Regression," Department of Economics, East Carolina University, located at <http://arts.uwaterloo.ca/~wnrr/Soc710_421/Whitehead%20Logistic%20Regression.ppt> (48 pages).

Willems, R. et al. (May 29, 1998). "Decrease in Nucleoside Diphosphate Kinase (NDPK/nm23) Expression During Hematopoietic Maturation," *The Journal of Biological Chemistry* 273(22):13663-13668.

Wu, J. et al. (Sep. 1996). "Fas Ligand Mutation in a Patient with Systemic Lupus Erythematosus and Lymphoproliferative Disease," *The Journal of Clinical Investigation* 98(3):1107-1113.

Wu, T. (2001). "Analysing Gene Expression Data from DNA Microarrays to Identify Candidate Genes," *Journal of Pathology* 195:53-65.

Xia, D. et al. (Sep. 2001). "Real-Time Polymerase Chain Reaction Analysis Reveals an Evolution of Cytokine mRNA Production in Allograft Acceptor Mice," *Transplantation* 72(5):907-914.

Yu, F. et al. (Oct. 1999). "Protein Synthesis-Dependent and Independent Induction of p69 2'-5'-Oligoadenylate Synthetase by Interferon-Alpha," *Cytokine* 11(10):744-750.

Zhang, L. et al. (Oct. 1997). "IRF-7, a New Interferon Regulatory Factor Associated with Epstein-Barr Virus Latency," *Molecular and Cellular Biology* 17(10):5748-5757.

Zhu, H. et al. (Nov. 2005). "The Role of Hyaluronan Receptor CD44 in MSC Migration in The Extracellular Matrix," *Stem Cells Express*, pp. 1-32.

Zucker, S. et al. (1999). "Increased Serum Stromelysin-1 Levels in Systemic Lupus Erythematosus: Lack of Correlation with Disease Activity," *Journal of Rheumatology* 26(1):7880.

Le Naour, F. et al. (May 25, 2001). "Profiling Changes in Gene Expression During Differentiation and Maturation of Monocyte-Derived Dendritic Cells Using Both Oligonucleotide Microarrays and Proteomics," *The Journal of Biological Chemistry* 276(21):17920-17931.

Lee, M.-T. et al. (Aug. 29, 2000). "Importance of Replication in Microarray Gene Expression Studies: Statistical Methods and Evidence from Repetitive cDNA Hybridizations," *Proceedings of the National Academy of Sciences* 97(18):9834-9839.

Legros-Maida, S. et al. (1994). "Granzyme B and Perforin Can Be Used as Predictive Markers of Acute Rejection in Heart Transplantation," *European Journal of Immunology* 24:229-233.

Li, B. et al. (Mar. 2001). "Noninvasive Diagnosis of Renal-Allograft Rejection by Measurement of Messenger RNA for Perforin and Granzyme B in Urine," *The New England Journal of Medicine* 344(13):947-954.

Liossis, S.-N. C. (Mar. 2001). "B-cell Kinase Lyn Deficiency in Patients with Systemic Lupus Erythematosus," *Journal of Investigative Medicine* 49(2):157-165.

Loftus, B. J. et al. (1999). "Genome Duplications and Other Features in 12 Mb of DNA sequence from Human Chromosome 16p and 16q," *Genomics* 60:295-308.

Magnusson, M. et al. (2001). "Importance of CpG Dinucleotides in Activation of Natural IFN-Alpha-Producing Cells by a Lupus-Related Oligodeoxynucleotide," *Scandinavian Journal of Immunology* 54:543-550.

Mansfield, E. S. et al. (2004). "Arraying the Orchestration of Allograft Pathology," *American Journal of Transplantation* 4:853-862.

Marcelin, A.-G. et al. (Nov. 2001). "Effects of Cyclosporine and Hydrocortisone on Kaposi's Sarcoma-Associated Herpesvirus Genome Replication and Cell Apoptosis Induction," *Transplantation* 72(10):1700-1703.

Marrack, P. et al. (2000). "Genomic-Scale Analysis of Gene Expression in Resting and Activated T Cells," *Current Opinion in Immunology* 12:208-209.

Metler, M. et al. (Nov. 2001). "Expression of the Chemokine Receptor CXCR3 and Its Ligand IP-10 During Human Cardiac Allograft Rejection," *Circulation* 104:2558-2564.

Mohler III, E. R. et al. (Jul. 1997). "Role of Cytokines in the Mechanism of Action of Amlodipine: The PRAISE Heart Failure Trial," *Journal of the American College of Cardiology* 30(1):35-41.

Morita, K. et al. (2001). "Early Chemokine Cascades in Murine Cardiac Grafts Regulate T Cell Recruitment and Progression of Acute Allograft Rejection," *The Journal of Immunology* 167:2979-2984.

Morris, D. L. et al. (Feb. 1997). "Immunophenotyping Analysis of Peripheral Blood, Splenic, and Thymic Lymphocytes in Male and Female Rats," *Journal of Pharmacological and Toxicological Methods* 37(1):37-46.

Neto, E. D. et al. (Mar. 2000). "Shotgun Sequencing of the Human Transcriptome with ORF Expressed Sequences Tags," *Proceedings of the National Academy of Sciences* 97(7):3491-3496.

Newton, M. A. et al. (2001). "On Differential Variability of Expression Ratios: Improving Statistical Inference about Gene Expression Changes from Microarray Data," *Journal of Computational Biology* 8(1):37-52.

Nickel, P. et al. (Sep. 2001). "Cytotoxic Effector Molecule Gene Expression in Acute Renal Allograft Rejection," *Transplantation* 72(6):1158-1161.

Oh, S.-I. et al. (Apr. 2001). "Correlation of Fas and Fas Ligand Expression with Rejection Status of Transplanted Heart in Human," *Transplantation* 71(7):906-909.

Perou, C. M. et al. (Aug. 2000). "Molecular Portraits of Human Breast Tumours," *Nature* 406:747-752.

Pickles, A. et al. (1995). "Latent-Class Analysis of Recurrence Risks for Complex Phenotypes with Selection and Measurement Error: A Twin and Family History Study of Autism," *American Journal of Human Genetics* 57:717-726.

Preble, O. T. et al. (Apr. 1982). "Systemic Lupus Erythematosus: Presence in Human Serum of an Unusual Acid-Labile Leukocyte Interferon," *Science* 216:429-431.

Pruitt, K. D. et al. (Jan. 2000). "Introducing RefSeq and LocusLink: Curated Human Genome Resources at the NCBI," *Trends in Genetics* 16(1):44-47.

Quattrone, A. et al. (1995). "Quantitation of bcl-2 Oncogene in Cultured Lymphoma/Leukemia Cell Lines and in Primary Leukemia B-Cells by a Highly Sensitive RT-PCR Method," *Haematologica* 80:495-504.

Raychaudhuri, S. et al. (May 2001). "Basic Microarray Analysis: Grouping and Feature Reduction," *Trends in Biotechnology* 19(5):189-193.

Rebouillat, D. et al. (Jan. 1999). "The 100-kDa 2',5'-Oligoadenylate Synthase Catalyzing Preferentially the Synthesis of Dimeric pppA2'p5'A Molecules Is Composed of Three Homologous Domains," *The Journal of Biological Chemistry* 274(3):1557-1565.

Ross, S. D. et al. (1999). "Reduced Neutrophil Infiltration Protects Against Lung Reperfusion Injury After Transplantation," *The Annals of Thoracic Surgery* 67:1428-1434.

Rus, V. et al. (Mar. 2002). "Expression of Cytokine- and Chemokine-Related Genes in Peripheral Blood Mononuclear Cells from Lupus Patients by cDNA Array," *Clinical Immunology* 102(3):283-290.

Saiura, A. et al. (Jul. 2001). "A Comparison of Gene Expression in Murine Cardiac Allografts and Isografts by Means DNA Microarray Analysis," *Transplantation* 72(2):320-329.

Salmon, J. E. et al. (Mar. 1996). "Fc-gamma-RIIA Alleles are Heritable Risk Factors for Lupus Nephritis in African Americans," *The Journal of Clinical Investigation* 97(5):1348-1354.

Schena, M. et al. (Oct. 1995). "Quantitative Monitoring of Gene Expression Patterns with a Complementary DNA Microarray," *Science* 270:467-470.

Schena, M. et al. (Oct. 1996). "Parallel Human Genome Analysis: Microarray-based Expression Monitoring of 1000 Genes," *Proceedings of the National Academy of Sciences* 93:10614-10619.

Schowengert, K. O. et al. (May 2000). "Increased Expression of the Lymphocyte Early Activation Marker CD69 in Peripheral Blood Correlates with Histologic Evidence of Cardiac Allograft Rejection," *Transplantation* 69(10):2102-2107.

Seiter, S. et al. (1998). "CD44 Variant Isoform Expression in a Variety of Skin-Associated Autoimmune Diseases," *Clinical Immunology and Immunopathology* 89(1):79-93.

Sharma, V. K. et al. (Dec. 1996). "Molecular Executors of Cell Death-Differential Intrarenal Expression of Fas Ligand, Fas, Granzyme B, and Perforin During Acute and/or Chronic Rejection of Human Renal Allografts," *Transplantation* 62(12):1860-1866.

Shin, Y. K. et al. (Apr. 2001). "Expression of Leukemia-Associated Antigen, JL1, in Bone Marrow and Thymus," *American Journal of Pathology* 158(4):1473-1480.

Shirali, G. S. et al. (May 2001). "Association of Viral Genome with Graft Loss in Children after Cardiac Transplantation," *The New England Journal of Medicine* 344(20):1498-1503.

Shoker, A. et al. (Aug. 2000). "Heightened CD40 Ligand Gene Expression in Peripheral CD4+ T Cells from Patients with Kidney Allograft Rejection," *Transplantation* 70(3):497-505.

Shou-Nee, S. et al. (1987). "Serum Interferon in Systemic Lupus Erythematosus," *British Journal of Dermatology* 117:155-159.

Shulzhenko, N. et al. (2001). "Monitoring of Intragraft and Peripheral Blood TIRC7 Expression as a Diagnostic Tool for Acute Cardiac Rejection in Humans," *Human Immunology* 62:342-347.

Shulzhenko, N. et al. (Nov. 2001). "Intragraft Activation of Genes Encoding Cytotoxic T Lymphocyte Effector Molecules Precedes the Histological Evidence of Rejection in Human Cardiac Transplantation," *Transplantation* 72(10):1705-1708.

Smith-Norowitz, T. A. et al. (Nov. 1999). "Lymphocyte Activation in Angina Pectoris," *Clinical Immunology* 93(2):168-175.

Staudt, L. M. et al. (2000). "Genomic Views of the Immune System," *Annual Review of Immunology* 18:829-859.

Stellrecht, C. M. et al. (1991). "Expression Pattern of a Hematopoietic Proteoglycan Core Protein Gene During Human Hematopoiesis," *Differentiation* 48:127-135.

Stites, D. P. et al. eds. (1991). *Basic and Clinical Immunology.* 7th Edition, Appleton & Lange: East Norwalk, CT, 6 pages. (Table of Contents).

Strehlau, J. et al. (Jan. 1997). "Quantitative Detection of Immune Activation Transcripts as a Diagnostic Tool in Kidney Transplantation," *Proceedings of the National Academy of Sciences* 94:695-700.

Supplemental Partial European Search Report mailed Jul. 9, 2007, for EP Application No. 01997055.7 filed Oct. 22, 2001, 6 pages.

Supplementary European Search Report mailed Oct. 18, 2007, for EP Application No. 03799755.8 filed Apr. 24, 2003, 17 pages.

Tamayo, P. et al. (Mar. 1999). "Interpreting Patterns of Gene Expression with Self-Organizing Maps: Methods and Application to Hematopoietic Differentiation," *Proceedings of the National Academy of Sciences* 96:2907-2912.

Tan, E. M. et al. (Nov. 1982). "The 1982 Revised Criteria for the Classification of Systemic Lupus Erythematosus," *Arthritis and Rheumatism* 25(2):1271-1277.

Tan, L. et al. (Mar. 2001). "Sequential Monitoring of Peripheral T-Lymphocyte Cytokine Gene Expression in the Early Post Renal Allograft Period," *Transplantation* 71(6):751-759.

Thomas, E. et al. (Jul. 2000). "Subtyping of Juvenile Idiopathic Arthritis Using Latent Class Analysis," *Arthritis & Rheumatism* 43(7):1496-1503.

Tibshirani, R. et al. (May 2002). "Diagnosis of Multiple Cancer Types by Shrunken Centroids of Gene Expression," *Proceedings of the National Academy of Sciences* 99(1):6567-6572.

European Search Report mailed Dec. 22, 2009, for EP Application No. 06770255.5 filed Dec. 5, 2007, 10 pages.

Japanese Office Action mailed Jan. 15, 2010, for JP Application No. 2003-587333 filed Apr. 24, 2003, English translation 4 pages.

U.S. Appl. No. 12/628,168, filed Nov. 30, 2009 for Lal et al.

U.S. Appl. No. 12/635,438, filed Dec. 10, 2009 for Wohlgemuth et al.

Yeung, K et al. (2004). "From co-expression to co-regulation: how many microarray experiments do we need?," *Genome Biology* 5(7):R48.

Deng, M. C. et al. (Jan. 2006). "Noninvasive discrimination of rejection in cardiac allograft recipients using gene expression profiling," *American Journal of Transplantation* 6(1):150-160.

European Search Report and Written Opinion mailed Apr. 28, 2010, for EP Application No. 08016970 filed Sep. 26, 2008, 10 pages.

Morgun, A. et al. (Feb. 1, 2001). "Cytokine and TLRC7 MRNA expression during acute rejection in cardiac allograft recipients," *Transplantation Proceedings, Orlando, Florida, USA* 33:1610-1611.

Nishimura, H. et al. (Aug. 1999). "Development of Lupus-like autoimmune diseases by disruption of the PD-1 gene encoding an ITIM motif-carrying immunoreceptor," *Immunity* 11(2):141-151.

Benner, S. A. et al. (Jul. 2001). "Evolution, Language and Analogy in Functional Genomics," *Trends in Genetics* 17(7):414-418.

Bennett, L. et al. (Mar. 17, 2003). "Interferon and Granulopoiesis Signatures in Systemic Lupus Erythematosus Blood," *The Journal of Experimental Medicine* 197(6):711-723.

Bergholdt, R. et al. (2000). "Characterization of New Polymorphisms in the 5' UTR of the Human Interleukin-1 Receptor Type 1 (IL1R1) Gene: Linkage to Type 1 Diabetes and Correlation to IL-1R1 Plasma Level," *Genes and Immunity* 1:495-500.

Centola, M. et al. (2006). "Genome-Scale Assessment of Molecular Pathology in Systemic Autoimmune Diseases Using Microarray Technology: a Potential Breakthrough Diagnostic and Individualized Therapy-Design Tool," *Scandinavian Journal of Immunology* 64:236-242.

Crow, M. K. et al. (2003). "Microarray Analysis of Gene Expression in Lupus," *Arthritis Research & Therapy* 5(6):279-287.

Dozmorov, M. G. et al. (2007). "$5\alpha$-Androstane-$3\alpha,17\beta$-Diol Selectively Activates the Canonical PI3K/AKT Pathway: A Bioinformatics-Based Evidence for Androgen-Activated Cytoplasmic Signaling," *Genomic Medicine* 1:139-146.

Horwitz, P. A. et al. (2004). "Detection of Cardiac Allograft Rejection and Response to Immunosuppressive Therapy with Peripheral Blood Gene Expression," *Circulation* 110:3815-3821.

Ing, N. H. (2005). "Steroid Hormones Regulate Gene Expression Posttranscriptionally by Altering the Stabilities of Messenger RNAs," *Biology of Reproduction* 72:1290-1296.

Invitation to Pay Additional Fees mailed Apr. 27, 2009, for PCT Application No. PCT/US2007/023675 filed Nov. 9, 2007, 6 pages.

Japanese Notice of Reasons for Rejection mailed on Apr. 27, 2009 for Japanese Patent Application No. 2004-549874 filed on Apr. 24, 2003, 9 pages. [English Translation only].

Japanese Notice of Reasons for Rejection mailed on May 26, 2009 for Japanese Patent Application No. 2003-587333 filed on Apr. 24, 2003, 6 pages. [English Translation, 9 pages.].

Kaufman, D. B. et al. (1997). "Functional Significance of Donor Islet Interleukin-1 Receptor Type 1 (IL-1Rt1) Expression in Islet Transplantation," *Transplantation Proceedings* 29:772-773.

Kirou, K. A. et al. (Dec. 2004). "Coordinate Overexpression of Interferon-?-Induced Genes in Systemic Lupus Erythematosus," *Arthritis & Rheumatism* 50(12):3958-3967.

Mandel, M. et al. (2006). "Gene Expression Studies in Systemic Lupus Erythematosus," *Lupus* 15:451-456.

Smith, A. D. et al. eds. (1997). *Oxford Dictionary of Biochemistry and Molecular Biology.* Oxford University Press, Oxford, New York, p. 618.

Tanaka, J. et al. (1995). "Cytokine Receptor Gene Expression in Peripheral Blood Mononuclear Cells During Graft-Versus-Host Disease After Allogeneic Bone Marrow Transplantation," *Leukemia and Lymphoma* 19:281-287.

U.S. Appl. No. 12/329,173, filed Dec. 5, 2008 for Wohlgemuth et al.

U.S. Appl. No. 12/544,182, filed Aug. 19, 2009 for Wohlgemuth et al.

U.S. Appl. No. 12/561,213, filed Sep. 16, 2009 for Wohlgemuth et al.

U.S. Appl. No. 12/584,615, filed Sep. 8, 2009 for Wohlgemuth et al.

U.S. Office Action mailed Dec. 4, 2008, for U.S. Appl. No. 11/223,492, filed Sep. 8, 2005, 18 pages.

U.S. Office Action mailed May 29, 2009, for U.S. Appl. No. 11/784,998, filed Apr. 9, 2007, 28 pages.

Vamvakopoulos, J. et al. (2002). "Genetic Control of IL-$1\beta$ Bioactivity Through Differential Regulation of the IL-1 Receptor Antagonist," *European Journal of Immunology* 32:2988-2996.

Zanders, E. et al. (2000). "Analysis of Immune System Gene Expression in Small Rheumatoid Arthritis Biopsies Using a Combination of Subtractive Hybridization and High-Density cDNA Arrays," *Journal of Immunological Methods* 233(1-2):131-140.

Eitner et al. (1998). "Chemokine Receptor (CXCR4) mRNA-Expressing Leukocytes are Increased in Human Renal Allograft Rejection," *Transplantation* 66(11):1551-1557.

U.S. Office Action mailed Jul. 22, 2010, for U.S. Appl. No. 11/433,191 filed May 11, 2006, 13 pages.

Wang et al. (2004). "Heart, but Not Skin, Allografts from Donors Lackin Flt3 Ligand Exhibit Markedly Prolonged Survival Time," *J Immunol.* 172:5924.

U.S. Office Action mailed Mar. 23, 2010 for U.S. Appl. No. 12/635,438 filed Dec. 10, 2009, 8 pages.

Extended European Search Report received for European Patent Application No. 07861283.5, mailed on Dec. 27, 2010, 17 pages.

Extended European Search Report received for European Patent Application No. 10157687.4, mailed on Oct. 28, 2010, 9 pages.

Non Final Office Action received for U.S. Appl. No. 12/628,168, mailed on Dec. 10, 2010, 35 pages.

Notice of Allowance received for U.S. Appl. No. 12/823,090, mailed on Jan. 25, 2011, 27 pages.

Non Final Office Action received for U.S. Appl. No. 12/985,314, mailed on Feb. 22, 2011, 73 pages.

Office Action received for Japanese Patent Application No. 2004-549874, mailed on Nov. 5, 2010, 13 pages (8 pages of English translation and 5 pages of Office Action).

Affymetrix Webstie, Available at: https://www.affymetrix.com/analysis/netaffx/showresults.affx, retrieved on Jan. 13, 2011.

Carow et al., "Expression of the Hematopoietic Growth Factor Receptor FLT3 (STK-1/Flk2) in Human Leukemias", Blood, vol. 87, No. 3, 1996, pp. 1089-1096.

Garraway et al., "Array-based Approaches to Cancer Genome Analysis", Drug Discovery Today: Disease Mechanisms, vol. 2, No. 2, 2005, pp. 171-177.

Hayashi et al., "Effects of Glucocorticoids on Gene Transcription", European Journal of Pharmacology, vol. 500, 2004, pp. 51-62.

Keshavjee et al., "Immunoregulatory Influences on Peripheral Blood Gene Expression in Lung Transplant Patients: The Lung Allograft Rejection Gene Expression Observational (LARGO) Study", The Journal of Heart and Lung Transplantation, 2006, p. S78.

Kronick, Mel N., "Creation of the Whole Human Genome Microarray", Expert Review Proteomics, vol. 1, No. 1, 2004, pp. 19-28.

Kuehn et al., "Identification of Steroid—Responsive Genes in Organ Cultured Human Eyes", Investigative Ophthalmology and Visual Science, vol. 46, 2005: E-Abstract 3709, pp. 1-2.

Mehra et al., "Gene Expression and Prediction of Early Cardiac Allograft Rejection: Discovery of a Gene-Based Corticosteroid Efficacy Measure", The Journal of Heart and Lung Transplantation, vol. 26, No. 2S, 2007, pp. S106-S107.

Mehra et al., "The Role of IL1R2 and FLT3 Gene Expression in Cardiac Allograft Rejection: A Precise Measure of Corticosteroid Effect?", Circulation, vol. 114, 2006, (2 pages of Abstract).

Mehra et al., "Transcriptional Signals of T-cell and Corticosteroid-Sensitive Genes are Associated with Future Acute Cellular Rejection in Cardiac Allografts", The Journal of Heart and Lung Transplantation, vol. 26, No. 12, 2007, pp. 1255-1263.

Su et al., "A Gene Atlas of the Mouse and Human Protein-Encoding Transcriptomes", Proceedings of the National Academy of Sciences, vol. 101, No. 16, 2004, pp. 6062-6067.

Vermeer et al., "An in Vitro Bioassay to Determine Individual Sensitivity to Glucocorticoids: Induction of FKBP51 mRNA in Peripheral Blood Mononuclear Cells", Molecular and Cellular Endocrinology, vol. 218, 2004, pp. 49-55.

Zeigler et al., "Cellular and Molecular Characterization of the Role of the FLK-2/FLT-3 Receptor Tyrosine Kinase in Hematopoietic Stem Cells", Blood, vol. 84, No. 8, 1994, pp. 2422-2430.

* cited by examiner

US 7,993,832 B2

METHODS AND COMPOSITIONS FOR DIAGNOSING AND MONITORING THE STATUS OF TRANSPLANT REJECTION AND IMMUNE DISORDERS

RELATED APPLICATIONS

This application claims benefit of U.S. Provisional Application Ser. No. 60/837,698, filed Aug. 14, 2006, which is incorporated herein by reference in its entirety.

TECHNICAL FIELD

The invention relates to methods and materials involved in diagnosing and monitoring the status of transplant rejection and immune disorders by using splice variants to improve the assessment of immunological or inflammatory activity in subject samples.

BACKGROUND OF THE INVENTION

The human immune system plays a defensive role in most immunological conditions, diseases, and disorders. However, it can also function adversely when cells, tissues, or organs are transplanted from one individual to another by attacking these allografts. In addition, certain autoimmune diseases are caused by inappropriate immune system response, where the immune system attacks the body's own cells, tissues, or organs. Thus, it is necessary to modulate immune response when a patient receives a transplant or suffers from an immune disorder, especially during the onset or flare of such disorders. Such modulation can involve changing or varying the amount of immunosuppressive drugs, usually steroids, administered to an individual in need of immunosuppression. After transplant or suppression of a flare, the dosage of immunosuppressant(s) is reduced as quickly as possible to prevent side effects and to preserve some immune response against infectious or opportunistic diseases.

In the months and/or years after transplant or onset of an immune disorder, the individual is usually monitored for tissue damage, dysfunction, or graft rejection. In heart transplant, for example, the heart muscle is biopsied by a surgeon and evaluated by a pathologist at least once a month for a year or more. Each biopsy is invasive, painful, and expensive; moreover, the biopsy is extremely localized, and histological abnormalities in any non-biopsied area of the heart are easily missed. In immune disorders and other transplants, biopsy and/or other assays are performed to detect changes in gene expression, metabolites, or proteins and to monitor the subject's immune response.

The role of leukocytes in immune disorders, especially rheumatic disorders such as systemic lupus erythematosus (SLE) and rheumatoid arthritis (RA), has become the focus of a great deal of research. These two diseases are both characterized by dysregulation of the immune system (causing damage to a variety of tissues and organs) and differential expression of genes in leukocytes (e.g., B-cells, granulocytes, monocytes, and T-cells) suggesting the use of these differentially expressed genes in diagnosing and monitoring immune disorders. However, definitive diagnosis and prediction of flares remain challenging despite recent advances in gene expression profiling (Baechler et al (2003) PNAS 100:2610-2615, Kirou et al (2004) Arthritis and Rheumatism 50:3958-3967, and Kirou (2005) Arthritis and Rheumatism 52:1491-1503).

While expression of a single gene can often be correlated with normal or abnormal function or status, the simultaneous measurement of differential expression in several genes greatly increases accuracy for detecting transplant rejection, steroid responsiveness, and disease activity. Furthermore, assaying gene expression in blood samples is far more comprehensive and less invasive than biopsy in determining transplant rejection (cf. Deng et al (2006) Am J Transplant 6:150-160) or diagnosing and monitoring the status of transplants and immune disorders.

There is a need in the art for improved diagnosis and monitoring of the status of transplants and immune disorders, especially transplant rejection or non-rejection, steroid responsiveness, and onset or flare of immune disorders. Preferred methods would utilize blood samples to further improve over existing techniques. The present invention provides methods for using splice variants of genes known to have utility in diagnosing and monitoring the status of transplants and immune disorders to improve diagnosis and monitoring of transplant rejection, steroid responsiveness, and onset or flare of immune disorders.

SUMMARY

The invention presents methods for using splice variants of genes known to detect transplant rejection or to diagnose immune disorders to improve diagnosis and monitoring of the status of transplant rejection or immune disorders. The invention also presents the use of splice variants, primers, primer sets, probes, amplicons, antibodies and affinity reagents that specifically detect the expression of the splice variant using nucleic acid and protein technologies, assays and diagnostic kits.

One aspect of the present invention is a method for diagnosing or monitoring the status of a transplant or an immune disorder by selecting a splice variant of a gene where the gene is known to have utility in diagnosing or monitoring the status of a transplant or immune disorder; detecting expression of the splice variant using a probe that specifically detects the expression of the splice variant; and diagnosing the status of a transplant or immune disorder based on the expression of the splice variant in the sample.

In certain embodiments of the method, transplant rejection or non-rejection in a patient and/or onset or flare of the immune disorder in a subject are diagnosed and monitored, efficacy of a therapeutic agent is determined, treatment administered to one or more patients with a transplant or subjects with an immune disorder is monitored, steroid or immunosuppressant responsiveness of one or more patients with a transplant or subjects with an immune disorder is assessed, a treatment plan for a patient with a transplant or a subject with an immune disorder is monitored, T cell activity is monitored, or acute cellular rejection is monitored.

In a second embodiment of the method, the probe is a primer or a primer set that specifically detects expression of the splice variant by generating an amplicon of the splice variant in a polymerase chain reaction (PCR). In a third embodiment, the probe is an antibody or affinity reagent that specifically detects expression of the splice variant by specifically binding an epitope of the splice variant. In a fourth embodiment, the splice variant encodes polypeptides such as ADM, CBLB, CD44, CXCR3, CXCR4, FASL, FLT3, G6B-1, IL1R2, ITGA4, ITGAM, ITGB7, LAIR2, MARCH8, OAS3, PDCD1, PRDM, PF4, RHOU, SEMA7A, WDR40A or ZNFN1A1 or fragments thereof. In preferred embodiments, the splice variants are CD44v1-1N, IL1R2V4-7N, LAIR2v2-2N, and PRDM1v1-2N. In a fifth embodiment, the transplant being monitored is an allograft of an artificial organ, a mechanical organ, bone marrow, a cornea, a heart, a kidney, a liver, a lung, an organ-system, a pancreas, pancreatic islet cells, stem cells, skin tissue, skin cells, or a xenotransplant. In a sixth embodiment, the immune disorder is acute respiratory distress syndrome, Addison's disease, allograft rejection, ankylosing spondylitis, Takayasu's arteritis, arteriosclerosis, asthma, atherosclerosis, congestive heart failure, primary sclerosing cholangitis, Churg-Strauss syndrome, CREST syndrome, Crohn's disease, ulcerative colitis, diabetes mellitus, emphysema, glomerulonephritis, Wegener's granulomatosis, Grave's disease, autoimmune hepatitis, Kawasaki's syndrome, systemic lupus erythematosus, multiple sclerosis, myasthenia gravis, myelofibrosis, pancreatitis, polyarteritis nodosa, polymyositis, psoriasis, Raynaud's disease, Reiter's syndrome, rheumatoid arthritis, scleroderma, primary biliary sclerosis, systemic sclerosis, sepsis, septic shock syndrome, Sjogren's disease, ankylosing spondylitis, primary thrombocythemia, Hashimoto's thyroiditis, systemic vasculitis, Whipple's disease, complications of cancer, viral infection, bacterial infection, fungal infection, parasitic infection, protozoal infection, helminthic infection, or trauma. In a seventh embodiment, expression of the splice variant is specifically detected using a probe in a nucleic acid technology or a protein technology to analyze a sample from each of one or more patients with a transplant or subjects with an immune disorder and one or more reference subjects.

In one preferred embodiment, the sample is a fluid such as ascites, bile, whole blood or a blood fraction, cerebrospinal fluid, lymph, media in which cells were grown, pus, semen, a soluble fraction of a cell preparation, sputum, and urine. In a second preferred embodiment, RNA or cDNA made from the RNA is isolated from each sample and used in an assay for diagnosing or monitoring transplant rejection or an immune disorder.

A second aspect of the invention is to use splice variants to design probes that can be used in assays or diagnostic kits to analyze a sample from each of one or more patients with a transplant or subjects with an immune disorder and one or more reference subjects, to diagnose or monitor the status of a transplant or an immune disorder, to determine efficacy of a therapeutic agent, to monitor treatment administered to one or more patients with a transplant or subjects with an immune disorder, to assess steroid or immunosuppressant responsiveness of one or more patients with a transplant or subjects with an immune disorder, to monitor progression or remission of an immune disorder or a treatment plan for a patient with a transplant or a subject with an immune disorder. In one embodiment, a method for making a probe that improves diagnosis or monitoring of the status of a transplant or an immune disorder comprises aligning the nucleic acid sequence of a splice variant with the nucleic acid sequence of its gene that is known to have utility in diagnosing or monitoring the status of a transplant or an immune disorder as obtained from nucleic acid databases; selecting a unique fragment or region of the splice variant to design and make a probe further having at least two oligonucleotides from about 15 bases to about 30 bases in length; analyzing the sequence of the amplicon delimited by the probe against nucleic acid databases to determine that the amplicon only aligns with the gene known to have utility in diagnosing or monitoring the status of a transplant or an immune disorder; performing quantitative real-time PCR with one or more reference samples using the probe for the splice variant and a 3' primer set for the gene to compare expression; and determining that the splice variant detected by the probe shows greater expression thereby improving diagnosis or monitoring of the status of a transplant or an immune disorder. In another embodiment, the probe is used diagnose or monitor transplant rejection or non-rejection based on the expression of a splice variants that encodes CD44, FLT3, IL1R2, LAIR2, MARCH8, PDCD1, PRDM1, WDR40A, or fragments thereof; to diagnose and monitor the onset or flare of the immune disorder based on expression of the splice variant which encodes FASL, IL1R2, OAS3, or fragments thereof wherein the immune disorder is systemic lupus erythematosus; to determine steroid or immunosuppressant responsiveness in a patient with a transplant or a subject with an immune disorder based on expression of the splice variant which encodes FLT3, IL1R2, or fragments thereof; to monitor T-cell activity in a sample of gastric mucosa from subject with an immune disorder or HIV based on expression of the splice variant of a gene which encodes CBLB, CD8, CXCR3, FASL, ITGB7, PDCD1, and fragments thereof; and to diagnose or monitor lung transplant patients for acute cellular rejection based on assays employing primers which are specific for CD44, CD59, CORO2A, IL1R2, LAIR2, and PRDM1, and fragments thereof. Splice variants CD44v1-1N, IL1R2V4-7N, LAIR2v2-2N, and PRDM1v1-2N are particularly preferred for diagnosis and monitoring of acute cellular rejection in lung transplant patients.

A third aspect of the invention is a method for diagnosing or monitoring the status of a transplant or an immune disorder in a subject by providing an array containing at least one amplicon selected from Table 1 or one antibody that specifically detects the expression of a splice variant of a gene that is known to have utility in diagnosing or monitoring status of a transplant or an immune disorder wherein the splice variant improves diagnosing or monitoring the status of a transplant or an immune disorder; contacting the array containing the amplicon with a sample containing nucleic acids from the subject or contacting the array containing the antibody with a sample having proteins from the subject; detecting complexes formed on the array between at least one amplicon and a nucleic acid or at least one antibody and a protein from the sample; and diagnosing or monitoring status of a transplant or an immune disorder in a subject based upon detection of complex formation.

A fourth aspect of the invention is a method for improving diagnosis or monitoring of the status of a patient with a transplant or a subject with an immune disorder by providing a probe that detects the expression of a gene that is known to have utility in diagnosing or monitoring of the status of a transplant or an immune disorder using a whole blood sample; detecting the expression of the gene with the probe in a blood sample fraction from one or more subjects with a transplant or immune disorder and from one or more reference subjects; and determining whether the use of the blood sample fraction improves diagnosing or monitoring the status of a transplant or an immune disorder as compared to the whole blood sample.

BRIEF DESCRIPTION OF THE TABLES

Table 1 shows the genes and proteins, primer sets, NCBI GI sequence identifier (NCBI, Bethesda Md.) for the splice variant, and amplicons (nucleotide start, stop and length) as referenced to NCBI GI sequence identifier.

Table 2 shows the average, median and statistical results of RT-PCR assays on validated rejection (R) and non-rejection (NR) samples from transplant patients using the primers and primer sets described in Table 1.

Table 3 shows comparative expression of the primer sets in different cellular fractions of normal control blood samples.

Table 4 shows the expression of splice variant versus 3' probes in the diagnosis and monitoring of acute cellular rejection in lung transplant patients.

DETAILED DESCRIPTION OF THE PREFERRED EMBODIMENTS

Definitions

Unless defined otherwise, all scientific and technical terms are understood to have the same meaning as commonly used in the art to which they pertain. In this application, the singular form "a", "an", and "the" includes plural references unless the context clearly dictates otherwise. For example, the term "an agent" includes a plurality of agents and mixtures thereof. For the purpose of this disclosure, the following terms are defined below.

"Amplification" refers to any device, method or technique that can generate copies of a nucleic acid. Amplification can, for example, be achieved using polymerase chain reaction (PCR) techniques such as linear amplification (cf. U.S. Pat. No. 6,132,997), rolling circle amplification, and the like. Further, amplification and detection can be combined as in TAQMAN Real-Time PCR (RT-PCR) using TAQMAN protocols and PRISM 7900HT Sequence Detection system and software (Applied Biosystems (ABI), Foster City Calif.).

"Array" refers to an ordered arrangement of at least two reagents—antibodies, nucleic acids or proteins—in solution or on a substrate where at least one of the reagents represents a control and the other, a sample of diagnostic or prognostic interest. The ordered arrangement insures that the size and signal intensity of each labeled complex, formed between at least one reagent and at least one nucleic acid or protein to which the reagent specifically binds, is individually distinguishable.

"Differential expression" refers to an increased or up-regulated or a decreased or down-regulated expression as detected by absence, presence, or a statistically significant change in the amount of messenger RNA (mRNA) or protein in a sample.

An "epitope" refers to an antigenic or immunogenic determinant, structural feature, or region of an oligopeptide, peptide, or protein that is capable of inducing formation of an antibody that specifically binds the protein.

A "gene expression profile" refers to the identification, characterization and representation of multiple genes expressed in a normal, diseased, or treated sample as measured using nucleic acid or protein technologies. Results from assays of subject or patient samples can be compared with reference gene expression profiles or can be analyzed using an algorithm that produces a result that indicates the status of the subject or patient.

"Immune disorder" includes any autoimmune or inflammatory complication, condition, disease or disorder including but not limited to acute respiratory distress syndrome, Addison's disease, allograft rejection, ankylosing spondylitis, Takayasu's arteritis, arteriosclerosis, asthma, atherosclerosis, congestive heart failure, primary sclerosing cholangitis, Churg-Strauss syndrome, CREST syndrome, Crohn's disease, ulcerative colitis, diabetes mellitus, emphysema, glomerulonephritis, Wegener's granulomatosis, Grave's disease, autoimmune hepatitis, Kawasaki's syndrome, systemic lupus erythematosus, multiple sclerosis, myasthenia gravis, myelofibrosis, pancreatitis, polyarteritis nodosa, polymyositis, psoriasis, Raynaud's disease, Reiter's syndrome, rheumatoid arthritis, scleroderma, primary biliary sclerosis, systemic sclerosis, sepsis, septic shock syndrome, Sjogren's disease, ankylosing spondylitis, primary thrombocythemia, Hashimoto's thyroiditis, systemic vasculitis, Whipple's disease, complications of cancer, viral, bacterial, fungal, parasitic, protozoal, and helminthic infections including HIV, and trauma and the like.

"Immunosuppressant" refers to any therapeutic agent that suppresses immune response—anticoagulents, antimalarials, heart drugs, non-steroidal anti-inflammatory drugs (NSAIDs), and steroids—including but not limited to Ace inhibitors, aspirin, azathioprine, B7RP-1-fc, β-blockers, brequinar sodium, campath-1H, celecoxib, chloroquine, corticosteroids, coumadin, cyclophosphamide, cyclosporin A, DHEA, deoxyspergualin, dexamethasone, diclofenac, dolobid, etodolac, everolimus, FK778, feldene, fenoprofen, flurbiprofen, heparin, hydralazine, hydroxychloroquine, CTLA-4 or LFA3 immunoglobulin, ibuprofen, indomethacin, ISAtx-247, ketoprofen, ketorolac, leflunomide, meclophenamate, mefenamic acid, mepacrine, 6-mercaptopurine, meloxicam, methotrexate, mizoribine, mycophenolate mofetil, naproxen, oxaprozin, Plaquenil, NOX-100, prednisone, methyprenisone, rapamycin (sirolimus), sulindac, tacrolimus (FK506), thymoglobulin, tolmetin, tresperimus, UO126, and antibodies including but not limited to alpha lymphocyte antibodies, adalimumab, anti-CD3, anti-CD25, anti-CD52 anti-IL2R, and anti-TAC antibodies, basiliximab, daclizumab, etanercept, hu5C8, infliximab, OKT4, and natalizumab.

"Labeling moiety" refers to any reporter molecule including fluorescent, chemiluminescent, or chromogenic agents, cofactors, enzymes, inhibitors, magnetic particles, radionuclides, reporters/quenchers, or substrates that can be attached to or incorporated into an antibody, nucleic acid or protein. Visible labels and dyes include but are not limited to anthocyanins, β glucuronidase, biotin, BIODIPY, Coomassie blue, Cy3 and Cy5, 4,6-diamidino-2-phenylindole (DAPI), digoxigenin, FAM/TAMRA, FITC, fluorescein, gold, green fluorescent protein, lissamine, luciferase, phycoerythrin, reporter/quencher pairs (HEX/TAMRA, JOE/TAMRA, ROX/BHQ2, TAMRA/BHQ2, TET/BHQ1, VIC/BHQ1, and the like), rhodamine, spyro red, silver, streptavidin, and the like. Radioactive markers include radioactive forms of hydrogen, iodine, phosphorous, sulfur, and the like.

"Modulation" refers to a change in the kind or amount of immunosuppressant given to a subject that results in a change in the subject's gene expression profile.

"Monitoring" refers to the detection of expression of a splice variant (at the nucleic acid or protein level) to provide useful information about an individual or an individual's health or disease status. Monitoring can include determination of prognosis, risk-stratification, selection of drug therapy, assessment of ongoing drug therapy, prediction of susceptibility, rejection or non-rejection, or disease activity, determining response to therapy, diagnosis of a disease or disease complication, following progression of a disease or providing any information relating to a patient's health status over time, selecting patients most likely to benefit from experimental therapies with known molecular mechanisms of action or where that mechanism can be important in a small subset of patients for which the medication does not have a label, screening a patient population to help decide on a more or less invasive or costly test, for example moving from a non-invasive blood test to a more invasive option such as biopsy.

"Nucleic acid technology" refers to any devices, methods and techniques that can be used to detect a nucleic acid including, but not limited to, northern analysis, PCR, RT-PCR, TAQMAN RT-PCR, FRET detection, and hybridization to an array containing cDNAs, genomic DNAs, oligonucleotide primers or primer sets, peptide nucleic acids, polynucleotides, RNAs, and the like of any length whether natural or synthetic.

"Patient" refers to an individual who can or has received any artificial, mechanical or natural transplanted cells, organs, or tissues from any animal or human source (including a subject's own transformed cells) that can be recognized by the immune system as foreign and activate an immune response or a subject who has been diagnosed with an immune disorder.

A "primer" refers to a reagent that can interact with a nucleic acid and serve as an initiation point for replication and/or transcription of the nucleic acid including, but not limited, to a cDNA, genomic DNA, RNA, or synthetic oligonucleotide that can be used with a detectable labeling moiety in solution or attached to a substrate to identify or quantitate gene expression. Further, two primers can be used in a "primer set" or "probe set" having at least one forward and at least one reverse primer that generates amplicon(s) for a gene or splice variant to detect gene expression.

"Probe" refers to any reagent including but not limited to primers, primer sets, amplicons, peptide nucleic acids, proteins, antibodies, affinity reagents, enzyme substrates, and the like that can be used to specifically detect expression of a splice variant for diagnosis and monitoring of the status of transplant and immune disorders "Protein technology" refers to any and all devices, methods and techniques that can be used to detect a peptide or polypeptide including but not limited to activity assays, affinity assays, antibody or protein arrays, chromatographic separation, colorimetric assays, two-dimensional gel electrophoresis, ELISA, fluorescent-activated cell sorting (FACS), mass spectrophotometric detection, protein-fusion reporter constructs, western analysis, and the like.

"Reference" refers to a validated, well-characterized normal control or diseased sample or values from gene expression profiles based on analysis of such samples taken from at least one subject and giving reliable test results whenever used in or with a particular nucleic acid or protein technology.

"Reference subject" refers to a subject whose sample is used as a reference in comparison to a subject with a transplant or an immune disorder to be diagnosed or monitored. An appropriate reference subject can be readily identified by one of ordinary skill in the art based upon the nature of the diagnosis or monitoring to be performed. For example, when determining utility of a splice variant in diagnosing transplant rejection, the reference subject can be a patient with a transplant that is not being rejected whereas the test subject has a transplant that is being tested for nonrejection (or vice versa).

"Sample" is used in its broadest sense and refers to any biological material obtained by any means from a subject and used in an assay e.g., to evaluate histology or to measure gene expression. A sample can include a fluid such as ascites, bile, blood, cerebrospinal fluid, lymph, pus, semen, sputum, urine and the like; the soluble fraction of a cell preparation, a fluid obtained by aspiration or lavage, or an aliquot of media in which cells were grown; a chromosome, an organelle, or membrane isolated or extracted from a cell; cDNA, genomic DNA, or RNA in solution or bound to a substrate; a cell; a tissue, a tissue biopsy, or a tissue print; buccal cells, skin, hair, a hair follicle, and the like. Preferred samples for diagnosis, prognosis, or monitoring of transplant rejection or immune disorders, or treatment thereof, are leukocytes from whole blood. Aspirated, biopsied or endoscopied samples from the sinuses, esophagus, stomach, small intestine, pancreatic duct, biliary tree, colon, bladder, bone marrow, kidney, ureter, prostate, breast, uterus, cervix, vagina and any other tissues or organs are also contemplated.

A "sampling means" refers to any and all means of obtaining a sample including but not limited to aspiration, biopsy, endoscopy, lavage, needle aspiration or biopsy, puncturing with a lancet; bleeding, ejaculating, expectorating, seeping or urinating into or onto a collection device, container, substrate, and the like.

"Specifically detecting expression of a splice variant" refers to detecting the differential expression of at least one splice variant of a gene at the level of nucleic acid or protein. For example, a primer set that detects one splice variant at a higher amount of expression than any other splice variants of a particular gene is specifically detected. Similarly, an antibody that binds an epitope of the splice variant but no other epitope of any protein is specifically detected.

"Splice variants" refers to nucleic acids and proteins that can be produced from a single gene and can have differences in sequence due to a variety of processes including but not limited to alternate selection of promoters which produce different 5' ends (and different N-termini of proteins), alternate selection of termination/polyadenylation sites which can produce different 3' ends (and different C-termini of proteins), and/or alternate splicing of exons and introns during mRNA-processing. The product of the splice variant can have unique protein structure, subcellular localization, biochemical processing or function due to additional, or fewer, domains than those present in other proteins produced from the gene.

"Status" refers to all biological and physiological aspects of a transplant or immune disorder including immune status. The status of a transplant recipient includes the degree and nature of immune-related complications such as cellular rejection (acute), humoral rejection, and chronic rejection (vasculopathy, chronic allograft nephropathy, bronchiolitis obliterans syndrome and the like); function including all parameters of the transplanted cell, tissue or organ and processes of a cell, tissue or organ targeted by the immune disorder, especially dysfunction associated with immunological response; and temporal aspects including but not limited to deterioration, improvement, progression, remission, or stability of a cell, a tissue, an organ, an allograft, a transplant patient, or a subject with an immune disorder. Status can be used to evaluate the need for administration of a therapeutic agent, to adjust dosage of such an agent, to change a treatment regimen, and the like.

"Steroid responsiveness" refers to expression of any gene that is affected by administration, or changes in administration, of one or more immunosuppressants, particularly steroids, or has a steroid-dependent regulatory element.

"Substrate" refers to any rigid or semi-rigid support to which antibodies, nucleic acids, peptides, polypeptides or proteins can be bound and includes magnetic or nonmagnetic beads, capillaries or other tubing, chips, fibers, filters, gels, membranes, microparticles, plates, polymers, slides, and wafers with a variety of surface forms including channels, columns, pins, pores, trenches, and wells.

"Therapeutic agent" refers to any pharmaceutical molecule or compound that has or can have a therapeutic effect upon a disease, condition or disorder. Typically a therapeutic agent will specifically bind to a nucleic acid or to an epitope of a protein and disrupt, modulate, or stabilize the activity of the nucleic acid or protein. The agent can be composed of inorganic and/or organic substances including carbohydrates, cofactors, fats, lipids, minerals, nucleic acids, and proteins, and used for the treatment of transplant related disorders including rejection or immune disorders including onset or flare of an immune disorder.

"Transplant" refers to any cell, tissue or organ allograft including, but not limited to, an artificial or mechanical organ, bone marrow, cornea, heart, kidney, liver, lung, pancreas, pancreatic islet, stem cell, skin, and xenotransplant.

"Validated" refers to a sample that has been assayed using a nucleic acid or protein technology or evaluated and/or graded by a pathologist and has a known condition, diagnosis or status; for example, a subject sample rated 3 or R that has a gene expression profile and/or histology that indicates active allograft rejection.

Description

The present disclosure provides methods for using splice variants of genes known to have utility in diagnosing and monitoring transplant rejection or immune disorders to improve the diagnosing and monitoring of transplant rejection or immune disorders, especially diagnosis and monitoring of transplant rejection or non-rejection, steroid responsiveness, and onset or flare of immune disorders by specifically detecting the expression of the splice variant. The present disclosure provides methods for selecting and testing splice variants that can be used for improved diagnosis and monitoring of transplant rejection or immune disorders by demonstrating that expression of the splice variant in assays on samples from patients with transplant rejection or subjects with immune disorders is greater than the expression of the gene.

The present disclosure also provides compositions that can be used in the improved methods disclosed. Reagents designed and expressed from the splice variants—primers, primer sets, peptide nucleic acids, and amplicons—are employed in assays using nucleic acid technologies, and antibodies that specifically bind an epitope of the splice variant but not any other epitope of any other protein or its splice variants are employed in assays using protein technologies to analyze normal control, patient and subject samples. The preferred samples for use with the disclosed methods are body fluids, particularly blood and its components which can be obtained by any sampling means.

RNA is isolated from normal control, patient and subject samples; and this RNA or equivalent cDNA, PNA, or synthetic nucleic acids constructed from or hybridizing with the RNA is used in the assays with the disclosed methods. Statistical analysis is used to establish correlations among the results from normal control, reference, patient and subject samples.

The reagents for use with the disclosed methods are also employed in diagnostic kits that can be used with a sample to monitor the status or treatment of a patient or subject to detect transplant rejection or nonrejection or steroid responsiveness, to diagnose an immune disorder, to determine efficacy of a therapeutic agent, and to design treatment regimens. In some cases, the kit further comprises an array.

Some of the splice variants of the genes and proteins were more responsive to immunosuppressants, particularly steroids, than their respective genes. Primers and primer sets used with the disclosed methods to amplify the splice variants showed improved detection, greater differential gene expression, in samples from transplant patients and subjects with immune disorders.

Source of Genes

Any gene that has utility for diagnosing and monitoring the status of transplants and immune disorders can be used in the methods disclosed herein. As discussed below, many genes have been demonstrated to have such utility. Any gene that has utility for diagnosing and monitoring the functional status of transplants and immune disorders can be used in the methods disclosed herein. As discussed below, many genes have been demonstrated to have such utility when used with 3' primers or primer sets in nucleic acid technologies. Methods disclosed herein for selecting splice variants and designing 5' primers and primer sets specific to the splice variant and upstream from the 3' primer can be applied to any and all of those genes. In addition, the methods disclosed can be applied to genes as they are identified as having utility for diagnosing and monitoring the status of transplants and immune disorders or even to genes that do not have known utility for diagnosing and monitoring the status of transplants and immune disorders.

Some splice variants have relatively rare expression in that they are cell specific and/or differentially regulated. The methods disclosed herein can be used to identify these rare, cell specific or differentially-regulated splice variants. In fact, the cell specific or differentially-regulated expression of a primer set based on 5' or unique sequence of a splice variant can be distinguished from expression of a primer set based on the 3' end of the gene that detects all variants that share the 3' end. These specific splice variants have improved diagnosis and monitoring of transplant rejection and immune disorders.

Differential gene expression of multiple genes is defined as a gene expression profile. Some profiles have already identified genes active in transplant rejection and immune disorders as described herein and in U.S. Pat. Nos. 6,905,827; 7,235,358; and 7,026,121; and U.S. Ser. Nos. 10/006,290; 10/990,298; 10/990,275; 10/511,937; 10/512,028; 11/433,191; 11/223,492; 11/784,998; 10/131,827 and 10/325,899; each of which is incorporated by reference herein in its entirety.

Reagents for molecular testing of samples from transplant patients or subjects with immune disorders are based on the genes disclosed in the patents and patent applications above and include but are not limited to the genes encoding ADM, CBLB, CD44, CD59, CORO2A, CXCR3, CXCR4, FASL, FLT3, G6B-1, IL1R2, ITGA4, ITGAM, ITGB7, LAIR2, MARCH8, OAS3, PDCD1, PF4, PRDM1, RHOU, SEMA7A, WDR40A, and ZNFN1A1 proteins shown in Tables 1-4. Gene expression profiles generated using these genes have been demonstrated to detect and predict transplant rejection or non-rejection as described in Deng et al (supra), prior to manifestation of physical symptoms or appearance of histological changes in endomyocardial biopsy (EMB) as described in U.S. provisional application No. 60/790,474 by Lal et al. (submitted 8 May 2006) entitled, "Steroid Responsive Nucleic Acid Expression and Prediction of Disease Activity", which is incorporated by reference herein in its entirety. Patients with gene expression scores<20 within 180 days of transplant (NPV) did not progress to rejection. NPV results were predictive for at least 12 week periods and indicate that patients in that group can be subjected to fewer EMBs and that post-operative steroid weaning can continue. In contrast, 58% of patients with a gene expression score>30 progressed to rejection. The expression of the steroid responsive genes encoding FLT3 and IL1R2 were particularly useful for detecting steroid responsiveness.

The reagents for use in the disclosed methods have been tested in many assays and have shown improved detection and monitoring of transplant non-rejection. It should be noted that it is particularly important to identify those patients meeting the criteria for non-rejection. With a diagnosis or determination of non-rejection, there is a decreased need for EMBs. As described in provisional application No. 60/790,474, the frequency and the total number of EMBs can be reduced for transplant patients showing non-rejection. This not only benefits the transplant patient who is subjected to fewer invasive and risky procedures, but also the hospital that can schedule the operating room for other operations, the surgeon who is released to other duties, and the insurance companies that will pay for fewer EMBs. These and other benefits are attributable to improved methods using blood samples for monitoring and treating transplant patients.

Interferon-inducible (INFi) genes such as those encoding FASL, IL-1R2, and OAS3 are known to be over-expressed in immune disorders such as systemic lupus erythematosus (SLE). FASL and IL-1R2 were shown to be over-expressed in microarray experiments using peripheral blood mononuclear cells (PMBC) of patients meeting American College of Rheumatology (ACR) criteria for SLE diagnosis (Baechler et al (2003) PNAS 100:2610-2615), and OAS3 was shown to be coordinately over-expressed with other INF-α inducible genes in RT-PCR experiments on PMBC of patients meeting ACR criteria for with SLE diagnosis (Kirou et al (2004) Arthritis and Rheumatism 50:3958-3967). Splice variants of INFi or INF-regulated (IFNr) genes can be used in RT-PCR assays on patient samples to screen for SLE, to predict flare, to assess immunosuppressant responsiveness, and to monitor the treatment regimen of an SLE patient.

CD44, CD59, CORO2A, IL1R2, LAIR2, and PRDM1 have been shown in Table 4 to be expressed in transplanted lung tissue during acute cellular rejection. Table 4 also showed that probes to specific the splice variants, CD44v1-1N, IL1R2V4-7N, LAIR2v2-2N, and PRDM1v1-2N, greatly improved the diagnosis or monitoring for acute cellular rejection in the blood of lung transplant patients.

Design and Use of Splice Variant Probes

As soon as one or more genes with utility in diagnosing and monitoring transplant rejection and immune disorders have been selected, the sequences for their splice variants are gathered from NCBI databases. After aligning the gene and its splice variants, one of skill in the art would use available software; for example, Primer Express software (ABI), to design primers or primer sets. It is understood that a probe includes any reagent capable of specifically identifying a nucleic acid of a given gene or splice variant, including but not limited to DNA, RNA, cDNA, PNA, synthetic oligonucleotide, and partial or full-length nucleic acid sequences. Further, an individual primer or primer set can correspond to one gene or splice variant, and multiple primers or primer sets can correspond to a single gene or splice variant. Such probes can be used in any combination in detecting the expression of a gene or splice variant. The expression of the gene or splice variant can be measured by using the primers or primer sets in any nucleic acid technology available to one of skill in the art including but not limited to RNA profiling, northern analysis, PCR, RT-PCR, TAQMAN analysis, FRET detection, hybridization to an array, molecular beacons, and the like.

One of skill in the art would analyze the protein expressed by the splice variant using protein technologies including but not limited to fluorescent activated cell sorting (FACS), enzyme assay, immunoassay, MRI imaging, nuclear imaging and the like. For example, protein expression in a sample can be evaluated by one or more methods selected from western analysis, two-dimensional gel analysis, chromatographic separation, mass spectrometry, protein arrays, and the like.

Methods for producing and evaluating antibodies produced against epitope(s) of the splice variant and used in protein technologies are well known in the art. Protein analysis software is available on the web from the Swiss Institute of Bioinformatics (Basel, Switzerland) or from commercial suppliers such as Invitrogen (Carlsbad Calif.). Antibodies and other affinity reagents can be prepared using methods well known in the art or obtained by providing the splice variant protein to any number of commercial ventures including Covance Research Products (Cumberland Va.), Fusion Antibodies (Belfast, Ireland), Strategic BioSolutions (Newark Del.), and the like. Additional details regarding the variety of immunological and immunoassay procedures adaptable to the present methods and compositions can be found in, e.g., Rose et al (1997; Manual of Clinical Laboratory Immunology, ASM Press), Auchincloss et al (1999; Transplantation Immunology, John Wiley & Sons Inc), and Paul (2003; Fundamental Immunology, 4th ed., Lippincott, Williams & Wilkins). Alternatively, affinity reagents including but not limited to antibodies and small molecules are available that recognize epitopes of the splice variant protein and are used in the assays described above, and especially with protein arrays, to detect the expression of particular proteins. For example, labeled affinity reagents are exposed to populations of leukocytes to detect a protein that is expressed on the cell surface of leukocytes. After binding the reagent, leukocytes expressing the protein are identified and counted using FACS.

One of skill in the art would select the appropriate method for measuring nucleic acid or protein expression based upon such factors as the kind of transplant or immune disorder, ease of measurement of each diagnostic gene, need for accuracy of measurement of each gene or splice variant, etc. When measuring expression of the protein, selection of technique will be dictated by the nature of the protein and particular differences between splice variants, e.g., activity assays are useful for enzymes, and fluorescent activated cell sorting is useful for membrane-bound and membrane-associated proteins. In certain embodiments, different techniques can be used to measure each gene or splice variant. In other embodiments, the same technique can be used to measure expression of all the genes and splice variants in a diagnostic set. In some embodiments, diagnostic probes are immobilized on a substrate.

Where primer sets detect expression by hybridization to nucleic acids, hybridization conditions can be highly stringent or less highly stringent, depending upon the required specificity. By way of example, where the primer set is hybridized to RNA samples including RNA samples that have been converted to DNA by reverse transcriptase and/or amplified, highly stringent conditions can refer to washing for a set time period such as 20 minutes in 6×SSC/0.05% sodium pyrophosphate at 37° C. (for 14-base oligos), 48° C. (for 17-base oligos), 55° C. (for 20-base oligos), and 60° C. (for 23-base oligos).

Reagents and Kits

Reagents for use with the disclosed methods can encompass 1) genes and splice variants, their primers, primer sets and amplicons that can be used in nucleic acid technologies, particularly quantitative RT-PCR, and 2) proteins, their fragments and antibodies that can be used in protein technologies, particularly arrays. The reagents can also be used in assays or kits to diagnose or monitor transplant rejection or immune disorders. The gene expression profile from a sample can be compared to validated or reference gene expression profiles to diagnose, monitor, determine transplant rejection or non-rejection, onset or flare of an immune disorder, efficacy of a particular therapeutic agent or immunosuppressant regimen, and the like.

Kits for diagnosing and monitoring the status of transplant patients or subjects with immune disorders using the improved methods for detecting expression of one or more splice variants, as described above, are also disclosed. Each kit includes instructions in human and/or machine readable form as well as the reagents typical for the assay used to detect expression of the one or more genes, splice variants or proteins. These can be, for example, nucleic acid or antibody arrays, primers or primer sets for RT-PCR, and the like that produce expression profiles for the genes, splice variants or proteins. The kits can also contain reagents for use with nucleic acid technologies including, for example, reverse transcriptase, reverse transcriptase primer, a corresponding PCR primer set, a thermostable DNA polymerase (such as Taq polymerase), and a labeling moiety. Such kits can also contain reagents such as stains, enzyme substrates, or secondary antibodies specific for a particular gene product and include accessory components such as buffer, blocking reagents (antibodies, milk, and the like), and/or detection enzymes such as horse radish peroxidase or biotin-avidin based reagents. Such kits can also include arrays of probes as defined herein for detecting or measuring the expression of genes and splice variants.

The present invention contains many preferred embodiments and includes material from patents, patent applications and other publications incorporated by reference in their entirety for all purposes, but especially for details in practicing the invention and known to those in the art.

EXAMPLES

Example 1

Patient and Validated Samples

Heart Transplant

Heart transplant data and samples were obtained as follows. After institutional review and approval, heart transplant patients at eight hospital centers gave informed consent and were included in transplant rejection studies (See Deng et al, supra). Patients were followed once a month for at least a year following heart transplant, and clinical data including reports on blood work, endomyocardial biopsies (EMBs), and immunosuppression were captured in electronic form. In general, EMBs are performed once a week for the first 30 days post-transplant; once every two weeks, from 31-90 days; once every four weeks, from 91-180 days; and once every 8 weeks, from 181-365 days. Electronic records, blood samples and EMB slides were obtained from the centers. The EMB slides were submitted to an independent panel of pathologists for interpretation according to the ISHLT criteria below. Reports from the centers, pathologist interpretations, and blood were analyzed to determine which genes were being expressed.

ISHLT (International Society for Heart and Lung Transplant) criteria for EMB was based on the histological scale: Grades 0, 1A, 1B, 2, 3A, 3B, or 4. In general, Grade 0 shows no histological evidence of rejection, but each successive grade has increased severity of leukocyte infiltration and/or damage. Although there can be variability in application of the ISHLT scale (between medical centers or individual pathologists or even between readings by the same pathologist at different times), variability was reduced by having the same pathologist(s) read and come to consensus on the ISHLT grade. It must also be noted that biopsy is not 100% sensitive or specific for diagnosing acute rejection due to small sample size and sample localization. However, the samples used herein were highly and specifically representative of Non-Rejection (NR)=Grade 0 and Rejection (R)=Grade 3+ categories.

Systemic Lupus Erythematosus (SLE)

SLE data and samples were obtained as follows. Patients who met the American College of Rheumatology (ACR) criteria for the diagnosis of SLE were identified (See Tan et al (1982) Arthritis Rheum 25:1271-7). After institutional review and approval, patients gave informed consent and were included in the Lupus Disease Activity Monitoring and Risk Stratification Archive Discovery Microarray Study. The samples and clinical data are available via the Autoimmune Biomarkers Collaborative Network (ABCoN).

Blood samples and clinical data were collected from two different studies. In the first, 32 samples were included in the analysis. Samples were derived from 15 patients with a clinical diagnosis of SLE, and the rest of the samples were derived from patients with RA or osteoarthritis (OA). Four samples were from subjects without known disease who served as controls. Samples from patients with SLE or RA were classified as "active" or "controlled" with respect to disease activity by the patient's physician based on objective and subjective criteria including patient history, physical exam and laboratory studies. An attempt was made to match SLE patients and controls with respect to use of medication, sex, age, and secondary diagnoses.

In the second, 299 patients were managed at Johns Hopkins Medical Center within the Hopkins Lupus Cohort, an ongoing, prospective study managed by Dr. Michelle Petri. In this cohort, all SLE patients were followed by protocol with visits at a minimum of every 3 months. A demographic survey (not shown) revealed that the cohort is more or less racially balanced, and its individuals represent a broad socioeconomic spectrum. The patient samples and clinical data were from SLE patients who had been in the cohort for more than one year with a total number of 1782 visits; the average number of quarterly visits was 5.9 for these patients.

Lung Transplant

Lung transplant patients who provided written informed consent were enrolled in the Lung Allograft Rejection Gene Expression Observational (LARGO) study. The LARGO study was initiated in 2004 to collect blood samples and clinical data from lung transplant patients at fourteen centers in five different countries and has been approved by the Institutional Review Board of each center.

All patients whose samples were used in these studies were at least 21 days post-transplant and had not been given blood transfusions or treated for rejection during the previous 21 days. No restrictions were placed on age, induction therapy, or CMV status. Patient blood was drawn and processed on the day the patient was evaluated for suspected rejection, hospitalized for transbronchial biopsy (TBB) or complications, or diagnosed with cytomegalovirus (CMV) infection. Clinical data were collected at each patient encounter and stored in the LARGO database.

TBBs were performed using standard techniques and graded by pathologists, blinded to the patient's clinical information, for histological evidence of rejection using the ISHLT scale: normal lung tissue (A0), minimal (A1), mild (A2), moderate (A3), and severe (A4). Tissue graded A2 or greater, a common threshold for therapeutic intervention, required the agreement of two out of three pathologists. Any sample≧A2 was treated as a rejection or R sample. Tissue graded A0 required consensus of all pathologists and was treated as a non-rejection or NR sample. All criteria were defined prior to the beginning of the study.

Example 2

Harvesting and Preparation of Blood Samples

The methods and procedures used to obtain and prepare the blood samples and the blood sample fractions are described. In one method, two tubes of blood were drawn from each patient or control subject using either a peripheral venous blood draw or directly from a large-bore intra-arterial or intravenous catheter inserted in the femoral artery or vein, subclavian vein or internal jugular vein. Care was taken to avoid sample contamination with heparin since it interferes with RNA preparation.

In a second method, eight ml of blood was drawn into a VACUTAINER PPT and/or CPT tubes (BD Biosciences (BD), San Jose Calif.) at the time of patient biopsy or evaluation as described herein. In some cases, control samples from healthy subjects were collected in CPT tubes, pooled and frozen for use in all experiments. In other cases, plasma diluted with PBS was collected from the CPT tubes. The CPT tube contained the anticoagulant sodium citrate, Ficoll Hypaque density fluid, and a thixotropic polyester gel barrier permeable upon centrifugation to red blood cells (RBCs) and granulocytes but not to mononuclear cells. The blood was mixed with the anticoagulant in the tube by inverting the tube 5-10 times. The mononuclear cells and plasma separated to the top of the tube while the RBCs and the granulocytes were trapped beneath the gel barrier when the tube was centrifuged in a swinging bucket rotor at 1750×g for 20 min at room temperature.

In one procedure, the mononuclear cells and plasma were decanted into a 15 ml tube, and 5 ml of phosphate-buffered saline (PBS) were added. The tubes were inverted 5 times and centrifuged for 5 min at 1750×g to pellet the cells. The supernatant was discarded.

In a second procedure, the clear plasma layer that formed above the mononuclear cell layer during centrifugation was aspirated and discarded. Then the mononuclear cell layer was aspirated, and all of the mononuclear cells were washed from the surface of the gel barrier with PBS. Approximately 2 mls of mononuclear cell suspension were transferred to a microcentrifuge tube and centrifuged in a microcentrifuge for 3 min at 16,000 rpm to pellet the cells. The supernatant was discarded.

In a third procedure, the blood cells from consenting normal control subjects were fractionated into specific subsets using cell separation kits and negative selection with antibodies prior to RNA isolation via the following protocols.

Platelets: Blood was collected into 8 ml VACUTAINER CPT tubes (BD) with sodium citrate. Blood from one tube was diluted with 8 ml Dulbecco's PBS (Invitrogen) with 2% fetal bovine serum (StemCell Technologies (SCT), Vancouver, Canada) and 0.5 mM ethylenediamine tetraacetic acid (PBSE). The diluted blood was centrifuged for 7 min at 850×g, and the platelet-rich plasma collected. Platelets were harvested by centrifuging at 1750×g for 5 min.

Erythrocytes: Peripheral blood mononuclear cells (PBMC) were prepared by centrifuging blood collected in VACUTAINER CPT tubes (BD) at 1750×g for 15 min. Cells and plasma above the barrier were suspended, diluted with 5 ml Dulbecco's PBS (Invitrogen), and harvested by centrifugation at 300×g for 12 min to reduce platelet contamination. Platelet-depleted PBMC was resuspended in PBSE and erythrocytes were enriched by glycophorin A-directed magnetic separation using EASYSEP Human Glycophorin A Depletion cocktail (SCT). Enriched erythrocytes were harvested by centrifugation at 1750×g for 5 min.

B-cells: B-cells were isolated from platelet-depleted PBMC by antibody-mediated magnetic separation using EASYSEP Human CD19 Selection cocktail (SCT). Enriched B-cells were pelleted by centrifugation at 1750×g for 5 min.

Granulocytes: Granulocytes were enriched by antibody-mediated magnetic removal of other cell types from platelet depleted PBMC using a custom cocktail of monoclonal antibodies to CD2, CD3, CD14, CD19, CD56, and glyocphorin A (SCT). After separation, the enriched granulocytes were harvested by centrifugation at 1750×g for 5 min.

Monocytes: Monocytes were isolated from platelet-depleted PBMC by antibody-mediated magnetic separation using EASYSEP Human CD14 Selection Cocktail (SCT). Enriched monocytes were pelleted by centrifugation at 1750×g for 5 min.

T-cells: T-cells were isolated from platelet-depleted PBMC by antibody-mediated magnetic separation using EASYSEP Human CD3 Selection Cocktail (SCT). Enriched T-cells were pelleted by centrifugation at 1750×g for 5 min. After each of the methods, procedures or protocols above, 1.8 ml of RLT lysis buffer (Qiagen) was added to the pellet; and the cells and lysis buffer were pipetted up and down to ensure complete lysis. Cell lysate was frozen and stored at −80 until total RNA was isolated. Normal control, patient, reference, and subject samples were prepared using these methods, procedures and protocols.

Example 3

Isolation of RNA

After blood samples were prepared, RNA was isolated from the samples of normal control subjects, transplant recipients, and subjects diagnosed with immune disorders—SLE, RA or OA—using several methods. In the first method: 1) samples were thawed, 2) 4 ml of chloroform were added to each tube, 3) tubes were vortexed prior to centrifugation at 2000×g for 5 min, and 4) the aqueous layer was moved to new tube and processed using the RNeasy Maxi kit (Qiagen) according to the manufacturer's instructions. RNA quality was assessed using spectrophotometry (A260/A280 spectrophotometric ratios were considered to be acceptable when they ranged between 1.6 and 2.0) and gel electrophoresis (when 2 µl of each sample were run on an agarose gel in the presence of ethidium bromide; no degradation of RNA and no DNA contamination were visible).

In the second method: 1) samples were thawed and held at room temperature for 5 min, 2) after adding 5 ml of chloroform, the samples were vortexed and incubated at room temperature for 3 min, 3) the aqueous layer was transferred to a new 50 ml tube and purified using the RNeasy Maxi kit (Qiagen), 4) the columns were eluted twice with 1 ml RNAse-free water and incubated for one min before each spin. RNAs isolated using the first and second methods were combined when the normal, control cell preparations demonstrated reproducibility. The RNAs were mixed in a 50 ml tube, aliquoted into two 15 ml storage or 1.5 ml microcentrifuge tubes (100 µl per tube), and stored at −80° C.

In the third method: total RNA was purified using the RNeasy Miniprep kit (Qiagen) according to the manufacturer's instructions. Cells were homogenized and DNAse treated on a QIASHREDDER columns (Qiagen) and purified RNA was eluted in 50 µl of water.

In the fourth method: RNA was prepared from the fractionated cell preparations by lysing the cell pellets in 600 µl RLT lysis buffer (Qiagen) and purifying the RNA with RNeasy Miniprep kits (Qiagen). RNA quality in later samples was tested using the Agilent 2100 bioanalyzer and RNA 6000 microfluidics chips (Agilent Technologies, Palo Alto Calif.).

Example 4 cDNA Synthesis cDNA was synthesized from the isolated RNA using reverse transcription with oligo-dT primers and random hexamers at a final concentration of 0.5 ng/µl and 3 ng/µl, respectively.

For the first strand reaction, 0.5 μg of mononuclear or cell-specific RNA or 2 μg of whole blood RNA and 1 μl of the OLIGO-dT primers/random hexamers (Invitrogen) were added to water in a reaction tube to a final volume of 11.5 μl. The tube was incubated at 70° C. for 10 min, chilled on ice, centrifuged, and 88.5 μl of first strand buffer mix (Invitrogen) was added to the tube.

The first strand buffer mix contained 1× first strand buffer, 10 mM DTT (Invitrogen), 0.5 mM dATP (New England Biolabs (NEB), Beverly Mass.), 0.5 mM dGTP (NEB), 0.5 mM dTTP (NEB), 0.5 mM dCTP (NEB), 200 U of SUPERSCRIPT RNAse H-reverse transcriptase (Invitrogen), and 18 U of RNAGUARD inhibitor (GE Healthcare (GEH), Piscataway N.J.). After the reaction was incubated at 42° C. for 90 min, the enzyme was heat-inactivated at 70° C. for 15 min. After adding 2 U of RNAse H (NEB) to the reaction tube, it was incubated at 37° C. for 20 min.

For second strand synthesis, 40 U of *E. coli* DNA polymerase (Invitrogen) and 2 U RNaseH (Invitrogen) were added to the previous reaction to bring the final volume to 150 μl. Salts and nucleotides were added to a final concentration of 20 mM Tris-HCl (pH 7.0; Fisher Scientific, Pittsburgh Pa.), 90 mM KCl (Teknova, Half Moon Bay Calif.), 4.6 mM MgCl2 (Teknova), 10 mM$(NH_4)_2SO_4$ (Fisher Scientific), 1× second strand buffer (Invitrogen), 0.266 mM dGTP, 0.266 mM dATP, 0.266 mM dTTP, and 0.266 mM dCTP.

After second strand synthesis for 150 min at 16° C., the cDNA was purified from the enzymes, dNTPs, and buffers using phenol-chloroform extraction followed by ethanol precipitation in the presence of glycogen. Alternatively, the cDNA was purified on a QIAQUICK silica-gel column (Qiagen) followed by ethanol precipitation in the presence of glycogen. The cDNA was centrifuged at >10,000×g for 30 min; and after the supernatant was aspirated, the pellet was washed with 150 ul of 70% ethanol. Following recentrifugation, the supernatant was removed, and residual ethanol was evaporated at room temperature. Alternatively, the volume of column purified cDNA was reduced in a vacuum evaporator to 7.4 μl.

Example 5

Designing and Selecting Primer Sets

Gene Primer and Probe Sets

Primers and primer sets were designed using the PRIMER3 program (Whitehead Research Institute (WRI), Cambridge Mass.). Default values were used for all parameters but melting temperature (Tm) and amplicon size. Tm was set at 61.7-63.7° C., and amplicon size, between 50 and 200 bases in length (optimum, about 100 bases). Salt concentration, a critical parameter affecting the Tm of the probes and primers, was left at the default, 50 mM.

The C source code for the PRIMER3 program was downloaded from the WRI website and complied on a Sun Enterprise 250 server (Sun Microsystems, Palo Alto Calif.) using the GCC compiler (Free Software Foundation, Boston Mass.). A subsequent version was compiled for machines running the Windows operating system (Microsoft, Redmond Wash.). The program was run from the command line which also dictated the use of an input file that contained the sequences and the parameters for primer design as described in the help files that accompanied the software. A script was written to input a number of sequences and automatically generate a number of potential primers. The following batch approach was used to design primers for the genes.

The first step in designing primers was to mask out repetitive sequences in the mRNA using the REPEATMASKER program (Institute for Systems Biology, University of Washington, Seattle Wash.). The second step was to mask out all known SNPs for the genes as annotated in the SNP database at NCBI (Bethesda Md.) that have an allelic heterozygosity higher than 1%. The masked sequence was submitted to PRIMER3 using the parameters outlined above, and the top eight sequences were selected. Alternatively, the PRIMER3 program was used on the MIT website (Massachusetts Institute of Technology, Cambridge Mass.) to examine a specific region on the mRNA of a particular splice variant. The final step was to test several of the top pairs of primers.

Gene Primers and Probe Sets

Generic, 3' primers and primer sets were designed and tested for each gene having utility in the diagnosis and monitoring of transplant rejection or an immune disorder. Splice variant primers and primer sets were also designed and tested for the splice variants of the proteins as shown in Table 1. The splice variant primer sets were 5' (or upstream) from the generic primers and chosen to span an exon-intron-exon junction of the splice variant or to amplify a feature or region of the sequence unique to the variant. Splice variant primer design specifically excluded repetitive sequence and probes to single nucleotide polymorphisms (as collated in the NCBI databases, NCBI), but neither emphasized nor avoided protein coding regions, functional domains, transcription start sites, 5' UTRs, 3' UTRs, polyadenylation signals, and the like. At least one unique feature distinguished each splice variant from other variants of the gene.

Several methods were used to find and analyze splice variants. One method used the ACEVIEW program (initially called Acembly) at NCBI which provides non-redundant annotation of the genes by co-aligning mRNA and EST sequences available in GenBank databases with genomic sequence. Sequences are clustered into the minimal number of alternative transcripts and genes and can be analyzed in terms of expression, intron-exon structure, alternative features, regulation and the like. Similarly, protein products are annotated via search for family membership, motifs, signals for subcellular localization, and the like. For the purpose of analyzing splice variants, they are described and depicted using the annotated mRNA(s) page at NCBI.

In another method, gene and splice variant sequences were downloaded from the GENE database and/or ACEVIEW (NCBI), and multiple alignments made using MAP (multiple sequence alignment program) on the websites of either Baylor College of Medicine (Houston Tex.) or Michigan Technical University (Houghton Mich.)

Unique regions and/or features in each splice variant identified by visual inspection were used with PRIMER3 software (WRI) to design primers for the splice variant-specific primer sets. Primers were ordered from Integrated DNA Technologies (Coralville Iowa).

Example 6

Testing of Primers and Primer Sets Using RT-PCR

Control genes: Variability in the RT-PCR measurements can be controlled by adding one or more control genes from bacteria, plants, or animals in one, two, three, four or more wells. Although human β-actin and β-GUS were used to validate the control RNAs, several other genes were also tested for variability between samples, for expression in mononuclear and whole blood RNA from control subjects and transplant recipients, on samples prepared using various methods, and in the RT-PCR assays. Based on criteria of low variability between control and patient samples and high expression across samples, β-actin, β-GUS, 18s ribosomal subunit, GAPDH, and 132-microglobulin were selected as the control genes and used in the various RT-PCR assays.

Primer Testing: Primers were tested once using standard RT-PCR protocol (without Rox or Sybr green dyes) to see whether they produced an amplicon of the correct size without amplifying nonspecific sequences. Each primer set was tested on cDNA made from mononuclear cell, normal control RNA described in Example 2. The PCR reaction contained 1× RealTime-PCR buffer (Ambion, Austin Tex.), 2 mM MgCl2 (ABI), 0.2 mM dATP (NEB), 0.2 mM dTTP (NEB), 0.2 mM dCTP (NEB), 0.2 mM dGTP (NEB), 0.625 U AMPLITAQ Gold enzyme (ABI), 0.3 µM of each primer to be used (Sigma Genosys, The Woodlands Tex.), 5 µl of the reverse transcription reaction, and water added to a final volume of 19 µl.

Following 40 cycles of PCR, melt curves for each PCR product were determined on a PRISM 7900HT Sequence Detection system (ABI), and primer pairs yielding a product with one clean peak were chosen for further analysis. One µl of product from each primer set assay was examined by agarose gel electrophoresis or using a DNA 1000 chip kit and an Agilent 2100 bioanalyzer (Agilent Technologies). From primer design and the genomic sequence, the expected size of the amplicon was known. Only primer pairs showing amplification of the single desired product, and minimal amplification of contaminants, were used in assays.

Primers were tested a second time to determine their efficiency in an RT-PCR reaction. cDNA was synthesized as described above. A set of 5 serial dilutions of cDNA in water: 1:10, 1:20, 1:40, 1:80, and 1:160 was tested using RT-PCR.

TAQMAN Setup: TAQMAN RT-PCR reactions were performed using the TAQMAN Universal PCR Master mix (ABI). The master mix was aliquoted into light tight tubes, one for each gene. The primer pair for each gene was added to the tube of PCR master mix labeled for that gene. A FAM/TAMRA dual labeled TAQMAN probe (Biosearch Technologies, Novato Calif.) was added to each tube. Alternatively, different combinations of commercially available fluorescent reporter dyes and quenchers can be used such that the absorption wavelength for the quencher matches the emission wavelength for the reporter. In one alternative, a Sybr green RT-PCR reaction can be performed using the TAQMAN PCR Reagent kit (ABI).

RT-PCR Assays and Analysis: 18 µl of master mix was dispensed into each well of a 384 well plate (ABI), and 2 µl of the template sample was dispensed into triplicate wells for each primer pair. The final concentration of each reagent was: 1×TAQMAN Universal PCR Master Mix, 300 nM each primer, 0.25 nM TAQMAN probe, and 2111 of 1:10 diluted template. PCR reactions were run on the PRISM 7900HT Sequence Detection system (ABI) with the following conditions: 10 min at 95° C.; 40 cycles of 95° C. for 15 sec, 60° C. for 1 min. Sequence Detection system software v2.0 (ABI) was used to analyze the fluorescent signal from each reaction. Standard deviation and coefficient of variation (CV) were calculated for triplicate wells. If the CV was greater than 2, an outlier among the three wells was identified and deleted; and the average was recalculated. In each plate, the difference in CT (ΔCT) was calculated for each gene control combination by subtracting the average CT of the gene from the average CT of the control. The expression relative to the control was calculated by taking two to the power of the ΔCT of the gene.

In each case, all plates were run in duplicate and analyzed in the same manner. The percent variation was determined for each sample and gene combination (relative expression, RE) by taking the absolute value of the RE for the second plate from the RE for the first plate, and dividing that by the average. If more than a quarter of the variation calculations on a plate were greater than 50%, then a third plate was run. The cycle number at which each amplification curve crossed CT was recorded, and the file was transferred to MS Excel for further analysis. CT values for triplicate wells were averaged, and data were plotted as a function of the $\log_{10}$ of the calculated starting concentration of RNA. The starting RNA concentration for each cDNA dilution was determined based on the original amount of RNA used in the reverse transcription reaction, the dilution of the reverse transcription reaction, and the amount used in the RT-PCR reaction (usually 5 µl). For each gene, a linear regression line was plotted through all points of the dilution series. The slope of the line was used to calculate efficiency of the reaction for each primer set using the equation, $E=10^{(-1/slope)}-1$. This efficiency equation was used to compare the expression of primer pairs or primer sets for each gene, and a primer pair was considered successful if the efficiency was reproducibly determined to be between 0.7 and 2.4.

Since variation of realtime PCR assays can arise from unequal amounts of RNA starting material, primer sets for control genes can be run in the reaction as the primer set for the gene or splice variant to reduce variation. Different fluorescent dyes were used to amplify the control, differentiating their expression from that of the gene or splice variant.

Example 7

Quantitative RT-PCR

Quantitative RT-PCR was used to compare the expression of each gene and its splice variants using the primers, cDNA synthesized from control, patient, reference, and subject RNAs, and reagents. cDNA was synthesized as described in Example 4.

Ten µl RT-PCR reactions were performed using an PRISM 7900 Sequence Detection system (ABI) using FAM-TAMRA labeled probes and standard TAQMAN protocols described above.

RT-PCR amplification product was measured as CT (threshold cycle=the point at which an amplification curve crosses a threshold fluorescence value) during the PCR reaction to observe amplification before any reagent became rate limiting. Threshold was set to a point where all of the reactions were in their linear phase of amplification. A lower CT indicated a higher amount of starting material (greater expression in the sample) since an earlier cycle number means the threshold was crossed more quickly. A CT of less than 30 based on appropriate cDNA dilutions provided linear results for blood samples.

In the alternative, other fluorescence methodologies can be used to measure amplification product in RT-PCR. Molecular beacons (Invitrogen) use FRET technology, and fluorescence is measured when a hairpin structure is relaxed by the specific probe binding to the amplicon. Other detection chemistries including ethidium bromide or other DNA-binding dyes and many modifications of the fluorescent dye/quencher dye can be used.

Example 8

Amplicons

The amplicons generated during RT-PCR by the primer sets for the genes and splice variants are set forth in Table 1. Amplicon size ranged from 72 to 196 basepairs in length.

The specificity of the primer sets was tested in silico to make sure that the primer sets would neither amplify any related genes in a gene family nor skew expression results. For example, the primer set for the splice variant, CXCR4v2-2, was tested using the BLAST program against the human REFSEQ database (NCBI) of all known human mRNAs. The blast report showed the expected alignment between the splice variant and the known CXCR4 gene, but no alignment with any stretch of nucleotides that would allow nonspecific amplification of related or non-related genes.

In addition, all amplicons of Table 1 were tested using either the BLAST or BLAT programs (Center for Biomolecular Science and Engineering, University of California, Santa Cruz Calif.). Only the blast report for MIRv3-2 showed any similarity to any other sequences in the genome. Since no amplification of non-specific sequences were found in RT-PCR assays using MIRv3-2, the blast report for MIRv3-2 appears to have identified pseudogenes.

Example 9

Reference Expression Profiles

In order to provide references for comparison, expression profiles were generated for normal control, transplant rejection, transplant non-rejection, SLE, RA, and OA samples. This was accomplished by performing assays using nucleic acid technologies with the primer sets and samples from one or more normal control subjects, from patients whose rejection or immune status had been previously tested and validated, or subjects who had been diagnosed and were symptomatic or being treated for a immune disorder. Assays were run on these samples, and the results of the assays were analyzed statistically and incorporated into a database of results. When expression profiles from patient or subject samples were compared with the references, the agreement with or deviation from the reference determined patient diagnosis or status.

Example 10

Comparison of Splice Variant Expression

The methods described above were applied to the genes/proteins described in Example 12. Splice variants for twelve of the genes were included in expression assays to determine their relative utility in diagnosing and monitoring the status of transplant patients and subjects with an immune disorder. The primers and probe sets for the genes and splice variants encoding ADM, CBLB, CD44, CD59, CORO2A, CXCR3, CXCR4, FASL, FLT3, G6B-1, IL1R2, ITGA4, ITGAM, ITGB7, LAIR2, MARCH8, OAS3, PDCD1, PF4, PRDM1, RHOU, SEMA7A, WDR40A and ZNFN1A1 proteins and fragments thereof were used to amplify isolated RNAs or cDNAs in samples from patients experiencing transplant rejection or nonrejection or diagnosed with an immune disorder. Only validated ISHLT non-rejection (NR=Grade 0) and rejection (R=Grade 3+ or A2) samples were used in these assays. Samples from 36 heart transplant subjects were rated R; from 35 subjects, NR; and from 7 subjects, normal control. Samples from 35 lung transplant subjects were rated R, and from 51 subjects, NR.

Heart Transplant Assays

In general, the primer sets for the splice variants were located further upstream toward the 5' end of the coding sequence and were chosen for a unique feature or region specific to the splice variant. The genes, primer sets and amplicons encoding and associated with ADM, CBLB, CXCR3, CXCR4, FASL, FLT3, G6B-1, IL1R2, ITGA4, ITGAM, ITGB7, MARCH8, OAS3, PDCD1, PF4, RHOU, SEMA7A, WDR40A and ZNFN1A1 proteins are set forth in Table 1 which shows the data on heart transplant subjects. Column 1 shows the NCBI name for the gene/protein; column 2, the name of each primer set (with the name of the generic or 3' probe listed first in the series associated with the name of a particular gene or protein); column 3, the NCBI GI sequence identifier of the sequence encoding the protein; column 4, the position of the first nucleotide of the amplicon generated during RT-PCR as located in the GI sequence identifier; and column 4, the position of the last nucleotide of the amplicon as located in the GI sequence identifier; and column 5, the number of basepairs in the amplicon generated by the primer set.

Primers were designed and tested as described in Example 6. The primers for the primer sets varied from about 15 to about 30 bases in length with a Tm of 61.7-63.7° C. at 50 mM salt; and they produce amplicons from about 72 to about 196 bases in length.

The primer sets for the genes and splice variants were used on validated samples in 64 quantitative RT-PCR assays as described in Examples 7-9. The data showing the expression of the gene and splice variant primer sets in at least 50 assays are shown in Table 2. Column 1 shows the name of the gene/protein; column 2, the name of the primer set; column 3 and 4, the average expression results on R and N samples; column 5 and 6, the median expression results on R and N samples; column 7, the ratio of expression results; column 8, T-test p-values from expression results; and column 9, improvement in T-test. Improvement in T-test was calculated using the value for the gene divided by the value for the splice variant. A ratio of one or less than (<) one indicates no improvement, but a value greater than (>) one means that use of the primer set for the splice variant improved detection.

Based on improvement in T-test, the probes sets for the splice variants, CXCR3v1-2, CXCR4v2-2, FLT3v3-1, IL1R2v4-7, ITGB7v1-6, MIRv3-2, and ZNFN1A1v5-3, performed better on validated samples than the generic primer sets in these assays. Primers or primer sets for the splice variants can be used in any assay using a nucleic acid technology to improve detection or monitoring of transplant rejection. More importantly, the primer sets for these splice variants can be substituted into any assay that used genes encoding CXCR3, CXCR4, FLT3, IL1R2, ITGB7, MARCH8, and ZNFN1A1 for detecting or monitoring the status of transplant rejection or immune disorders. Similarly, splice variants of the steroid responsive genes, FLT3 and IL1R2, can be substituted into any assay to improve detection and monitoring of steroid responsiveness, prediction of transplant rejection or non-rejection, and diagnosis and monitoring of SLE.

The gene and splice variant primer sets were also used in RT-PCR assays on the erythrocytes, B-cells, granulocytes, monocytes, platelets, and T-cells fractionated from peripheral blood drawn from seven normal control subjects. The fractionation procedures and RNA isolation are described in Example 2. Table 3 compares gene expression produced by the gene and splice variant primer sets in RT-PCR assays. Column 1 shows the name of the gene/protein; column 2, the name of the primer set; columns 3-6 show the name of the fractionated cell types that were assayed—column 3, B-cells; column 4, Granulocytes; column 5, Monocytes, column 6, T-cells, and column 7, Other cell types; and column 8, comparative expression and/or comments about expression.

The cell fractionation assays showed that the splice variants were expressed in the same cell type(s) as their respective genes, but in some cases, the expression using the splice variant primer set improved upon that of the original primer set. In fact, as shown in the last column of Table 3, the primer sets for CXCR3v1-2, CXCR4v2-2, TNFSF6v2-8, IL1R2v4-7, and MIRv5-1 splice variants improved upon the results obtained using the generic or 3' primer sets for CXCR3, CXCR4, FASL, IL1R2, and MARCH8, respectively.

In addition, the splice variants of CBLB, CXCR3, FASL, ITGB7, and PDCD1 that are expressed in T-cells are important in regulating the activation, migration, and function of T-cells. Probes for CBLB, CXCR3, FASL, ITGB7, and PDCD1 splice variants can be used in assays with or without other T-cell specific genes and proteins such as CD8 to provide an indication of T-cell activities related to transplant rejection, virus infections including HIV, and onset or flare of immune disorders. The splice variants and reagents therefrom can be substituted into assays to detect the presence, abundance, or activity of T-cells in the gastric mucosa of a patient diagnosed with HIV, to assess the efficacy of immunosuppressants or other therapeutic agents on T-cells, or to monitor treatment regimens of patients with fluctuating T-cell populations.

Example 11

Statistical Analysis

Methods for analyzing gene expression use an algorithm to evaluate data for a particular parameter and/or under a particular set of conditions to identify "groups" that share that parameter or express under those conditions. Statistical analyses were used on array and PCR data to define a set of genes that detected transplant rejection, evaluated gene expression for steroid responsiveness, and predicted transplant rejection when used with RT-PCR. The statistical behavior of an initial set of genes was used to identify other genes and splice variants with similar or greater expression under a set of conditions; and after cross-validation, these genes and splice variants were included in, or substituted into, the diagnostic set.

Classification algorithms, software and programs including, but not limited to, analysis of variance, classification and regression trees (Brieman et al. (1984) *Classification and Regression Trees*, Wadworth, Belmont Calif.), linear discriminatory analysis (Statsoft, Tulsa Okla.), multiple additive regression trees (Friedman (2002) Stanford University, Stanford Calif.), nearest shrunken centroids classifier (Tibshirani et al. (2002) PNAS 99: 6567-6572), significance analysis of microarrays (Tusher et al. (2001) PNAS 98: 5116-5121), one and two tailed T-tests, Wilcoxon's signed ranks test, and the like that can be applied to all types of PCR and array expression data and are described in the patents referenced and incorporated herein.

Example 12

Descriptions of the Proteins

The following list of nineteen genes are known to have utility in diagnosing and monitoring the status of transplant and immune disorders and were used in the Examples.

ADM maps to chromosome 11p15.4 and is a vasoactive peptide that is implicated in stimulating cell proliferation, inhibiting apoptosis, reducing blood pressure, and suppressing myocardial hypertrophy. ADM is known to be expressed in diabetes, hyperparathyroidism, nephropathy, pulmonary disease, and schizophrenia.

CBLB maps to 3q13.11 and is implicated in immune response where it interacts with CTLA-4 in diabetes, mediates NF-β activity through PI3K, and plays a negative role in activation of PAK, LFA-1 activation of T-cells, and FcERI-mediated activation of mast cells.

CD44 maps to 11pter-p13 and is an integral cell membrane glycoprotein with a postulated role in matrix adhesion lymphocyte activation and lymph node homing.

CD59 maps to locus 11p13 and is a novel membrane inhibitor of the membrane attack complexes expressed on most leukocytes and erythrocytes, indicating that it may have a role in preventing complement attack in the circulation.

CORO2A maps to locus 9q22.3, consists of 2 putative exons that encode a 525-amino acid polypeptide with homology to several actin-binding proteins, contains 5 WD repeats, and is expressed as a 5-kb message in brain and several other human tissues and as a 2-kb message in epidermis.

CXCR3 (also known as GPR9) maps to chromosome Xq13, is a seven-transmembrane receptor that contains at least one intron, and binds various chemokines that regulate the trafficking of immune cells during inflammatory response. CXCR3 is expressed on B, endothelial, and Th1 cells in subjects with asthma, diabetes, leukemias, and lymphomas. IFN-i protein 10 and IFN-induced monokine-2 bind the CXCR3 receptor.

CXCR4 (also known as fusin and NPY3R) maps to chromosome 2q21, has at least one intron, and functions in inflammatory reactions including microbial defense and viral invasion. Expression of CXCR4 mediates the migration of leukocytes and hematopoietic progenitors in the immune and central nervous systems, is found in various cancers, and is associated with HIV1 entry into cells.

FASL (also known as TNFSF6) maps to chromosome 1q23 and is implicated in immune response, cell-cell signaling, induction of apoptosis, positive regulation of the I-Kβ kinase/NF-Kβ cascade, and is up-regulated during acute kidney rejection episodes.

FLT3 (also know as STK1 and FLK2) maps to chromosome 13q12 and is responsive to corticosteroids. Its expression is associated with lymphohematopoietic stem cells particularly important in bone marrow transplant.

G6B maps to 6p21.33, is a member of immunoglobulin superfamily, contains six exons packed between two sets of repetitive elements, and effects platelet function and signal transduction.

IL1R2 (also known as IL1RB) maps to chromosome 2q12-q22, has at least two variants with no signaling properties, and inhibits IL1 activity by acting as a decoy or scavenger for IL1. IL1R2 is responsive to corticosteroids, and its expression has been reported in patients with arthritis, chronic fatigue syndrome, endometriosis, immune defense of eye tissues, pancreatitis, and pre-term delivery.

ITGA4 (also known as CD49d) maps to chromosome 2q31-q32, belongs to the integrin family, and is expressed on the surface of activated T-lymphocytes and monocytes. It has been implicated in the adhesion of these cells to endothelium and in the autoimmune response of multiple sclerosis and Crohn's disease.

ITGAM (also known as CR3A, Mac1, MO1 and CD11B) maps to chromosome 16p11.2, is responsive to corticosteroids, and is found on the surface of leukocytes where it functions in cell adhesion through the integrin-mediated signaling pathway.

ITGB7 maps to chromosome 12q13.13, is expressed on the surface of leukocytes where it plays a role in adhesive interactions in inflammatory and immune responses, and activation allows T-cells to migrate to non-lymphoid sites such as the intestine.

LAIR2 is an inhibitory receptor of the immunoglobulin superfamily associated with NK cells, contains one immunoglobulin-like domain, and although 84% homologous to LAIR1, lacks both a transmembrane and a cytoplasmic domain suggesting that it is secreted.

MARCH8 is an E3 ubiquitin ligase with a membrane-associated ring finger (C3HC4) motif that maps to chromosome 10q 11.21 and functions in erythropoiesis and as a cellular modulator of immune recognition.

OAS3 (also known as p100) maps to chromosome 12q24.2, is characterized by its capacity to catalyze the synthesis of 2',5' oligomers of adenosine (2-5As), to be INF-induced during viral infections, and to be differentially expressed in SLE distinguishing it from other immune disorders and, in particular, other rheumatic diseases such as rheumatoid arthritis (cf. U.S. Pat. No. 6,905,827, incorporated by reference herein in its entirety).

PDCD1 (also known as PD1) maps to chromosome 2q37.3 and is a cell surface receptor involved in immunomodulation, inhibiting autoreactive cells, and preserving self-tolerance. PDCD1 is expressed in programmed cell death and inhibits T-cell activity. Dysfunction of PDCD1 leads to the chronic lymphocyte hyperactivity characteristic of SLE.

PF4 (also known as CXCL4 and SCYβ4) maps to chromosome 4q12-q13, is a chemokine that contains three exons, is released from the α-granules of activated platelets, and binds with high affinity to heparin. PF4 is a strong chemoattractant for neutrophils and fibroblasts and has a role in both inflammation and wound repair.

PRDM1 maps to locus 6q21-q22.1, is required for the transient induction of the beta-interferon gene by virus, contains both positive and negative regulatory sequences, and may contribute to the terminal differentiation of B lymphocytes.

RHOU (also known as ARHU) maps to chromosome 1q42.11-q42.3 and is a member of the RHO family low molecular weight GTP-binding proteins known to be expressed in the stomach and small intestine. RHOU can activate PAK1 and JNK1, mediate the effects of WNT1 signaling on cell division, and function in cell migration.

SEMA7A (also known as SEMAL, SEMAK, and CDW108) maps to chromosome 15q22.2-q23, contains at least 13 exons, and is a GPI-anchored membrane-bound semaphorin. SEMA7A is expressed on the cell surface of activated T-lymphocytes and erythrocytes that function in the immune and nervous systems in association with integrin receptors and activation of MAPK signaling pathways.

WDR40A contains a WD40 domain and functions in erythropoiesis, regulating signal transduction, and processing pre-mRNAs.

ZNFN1A1 (also known as IKAROS or LYF1) maps to chromosome 7p12 and is a lymphoid restricted zinc finger transcription factor with at least eight splice variants. ZNFN1A1 is expressed in bone marrow, lymph node, peripheral blood leukocytes, spleen, and thymus, binds CD8 regulatory elements, is involved in hematopoiesis, endocrine and immune system development where it is required for the development and differentiation of all lymphoid lineages.

Example 13

Protein Expression

Adapter sequences for subcloning are added at either end of a coding region specific to the sequence for the gene or splice variant, or a portion thereof, and amplified using PCR. An epitope or affinity tag (6×his) can be added to facilitate purification and/or detection of the protein. The amplified cDNA is inserted into a shuttle vector that can replicate in bacteria, insect, yeast, plant, or mammalian cells. Such vectors typically contain a promoter that operably links to the coding region, replication start sites, and antibiotic resistance or metabolite selection sequences, and can have sequences for secretion from the cell.

The expression vector can be also used in an in vitro translation system or to transform cells. For example, Spodoptera frugiperda (Sf9) insect cells are infected with recombinant *Autographica californica* nuclear polyhedrosis virus (baculovirus). The polyhedrin gene is replaced with the cDNA by homologous recombination, and the polyhedrin promoter drives transcription. The protein is synthesized as a fusion protein with an affinity tag that enables purification.

Clones are analyzed to ensure that the inserted sequence is expressed. Once expression is verified, transformed cells are grown under selective conditions; and the protein is isolated from cells, or if secreted, from the growth media using chromatography, size exclusion chromatography, immunoaffinity chromatography, or other methods including cell fractionation, ion exchange, or selective precipitation.

The isolated and purified protein is then used as a reagent on an array or as an antigen to produce specific antibodies.

Example 14

Antibody Production and Testing

If antibodies are to be used as reagents, the sequence of the gene or splice variant is analyzed to determine regions of high immunogenicity (LASERGENE software; DNASTAR, Madison Wis.), and an appropriate oligopeptide is synthesized and conjugated to keyhole lympet hemocyanin (KLH) (Sigma-Aldrich, St Louis Mo.).

Immunization

Rabbits are injected with the oligopeptide-KLH complexes in complete Freund's adjuvant, and the resulting antisera is tested for specific recognition of the protein or fragments thereof. Antisera that react positively with the protein are affinity purified on a column containing beaded agarose resin to which the synthetic oligopeptide has been conjugated (SULFOLINK kit; Pierce Chemical, Rockford Ill.). The column is equilibrated using 12 ml IMMUNOPURE Gentle Binding buffer (Pierce Chemical). Three ml of rabbit antisera is combined with one ml of binding buffer and poured into the column. The column is capped (on the top and bottom), and antisera is allowed to bind with the oligopeptide by gentle shaking at room temperature for 30 min. The column is allowed to settle for 30 min, drained by gravity flow, and washed with 16 ml binding buffer (4×4 ml additions of buffer) . The antibody is eluted in one ml fractions with IMMUNOPURE Gentle Elution buffer (Pierce Chemical), and absorbance at 280 nm is determined. Peak fractions are pooled and dialyzed against 50 mM Tris, pH 7.4, 100 mM NaCl, and 10% glycerol. After dialysis, the concentration of the purified antibody is determined using the BCA assay (Pierce Chemical), aliquoted, and frozen.

Electrophoresis and Blotting

Samples containing protein are mixed in 2× loading buffer, heated to 95° C. for 3-5 min, and loaded on 4-12% NUPAGE Bis-Tris precast gel (Invitrogen). Unless indicated, equal amounts of total protein are loaded into each well. The gel is electrophoresed in 1×MES or MOPS running buffer (Invitrogen) at 200 V for approximately 45 min on an XCELL II apparatus (Invitrogen) until the RAINBOW marker (GEH) resolves and the dye front approaches the bottom of the gel. The gel is soaked in 1× transfer buffer (Invitrogen) with 10% methanol for a few minutes; and a PVDF membrane (Millipore, Billerica Mass.) is soaked in 100% methanol for a few seconds to activate it. The membrane, the gel, and supports are placed on the TRANSBLOT SD transfer apparatus (Biorad, Hercules Calif.) and a constant current of 350 mA is applied for 90 min.

Conjugation with Antibody and Visualization

After the proteins are transferred to the membrane, it is blocked in 5% (w/v) non-fat dry milk in 1× phosphate buffered saline (PBS) with 0.1% Tween 20 detergent (blocking buffer) on a rotary shaker for at least 1 hr at room temperature or at 4° C. overnight. After blocking, the buffer is removed, and 10 ml of primary antibody in blocking buffer is added and incubated on the rotary shaker for 1 hr at room temperature or overnight at 4° C. The membrane is washed 3 times for 10 min each with PBS-Tween (PBST), and secondary antibody, conjugated to horseradish peroxidase, is added at a 1:3000 dilution in 10 ml blocking buffer. The membrane and solution are shaken for 30 min at room temperature and washed three times for 10 min with PBST.

The wash solution is carefully removed, and the membrane is moistened with ECL+ chemiluminescent detection system (GEH) and incubated for approximately 5 min. The membrane, protein side down, is placed on x-ray film (Eastman Kodak, Rochester N.Y.) and developed for approximately 30 seconds. Antibody:protein complexes are visualized.

Example 15

Arrays

Arrays can be used to diagnose and monitor the status of transplant and immune disorders, especially to detect steroid responsiveness, to detect or diagnose transplant rejection or immune disorders, and to predict transplant rejection or the onset or flare of immune disorders. In one format, the array contains reagents specific for at least two genes or proteins, one that binds to a gene or splice variant or a product thereof, and one that binds to a control gene or a product thereof. These arrays can be produced using amplicons of Table 1, bacteria containing amplicons for the genes disclosed in U.S. Pat. Nos. 6,905,827; 7,235,358; and 7,026,121; and U.S. Ser. Nos. 10/006,290; 10/990,298; 10/990,275; 10/511,937; 10/512,028; 11/433,191; 11/223,492; 11/784,998; 10/131,827 and 10/325,899 or their splice variants including but not limited to those encoding ADM, CBLB, CXCR3, CXCR4, FASL, FLT3, G6B-1, IL1R2, ITGA4, ITGAM, ITGB7, MARCH8, OAS3, PDCD1, PF4, RHOU, SEMA7A, WDR40A and ZNFN1A1, or antibodies that form a specific complex with the proteins or fragments thereof encoded by the genes or their splice variants.

Amplicon Arrays

The amplicons are harvested from PCR reactions, purified using Sephacryl-400 beads (GEH) and ligated into a vector that is inserted into a bacterial cell. In a first method, bacterial cells containing individual clones are robotically picked and arranged on a nylon membrane. The membrane is placed on LB agar containing a selective agent (carbenicillin, kanamycin, ampicillin, or chloramphenicol depending on the vector used) and incubated at 37° C. for 16 hr. The membrane is removed from the agar and sequentially placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is UV irradiated, washed in 0.2% SDS at room temperature and rinsed three times in distilled water. Non-specific binding sites on the array are blocked by incubation in 0.2% casein in PBS for 30 min at 60° C., and the arrays are washed in 0.2% SDS and rinsed in distilled water. Alternatively, purified amplicons are arranged on a membrane manually or using a dot/slot blotting manifold and suction device (Biorad) and are immobilized by denaturation, neutralization, and UV irradiation as described above.

Purified amplicons are robotically arranged and immobilized on polymer-coated glass slides using the procedure described in U.S. Pat. No. 5,807,522 (which is hereby incorporated in its entirety). Polymer-coated slides are prepared by cleaning glass microscope slides (Corning Life Sciences, Corning N.Y.) by ultrasound in 0.1% SDS and acetone, etching in 4% hydrofluoric acid (VWR Scientific Products, West Chester Pa.), coating with 0.05% aminopropyl silane (Sigma-Aldrich) in 95% ethanol, and curing in a 110° C. oven. The slides are washed extensively with distilled water between and after treatments.

Probe Preparation for Membrane Hybridization cDNAs are prepared from patient blood samples; diluted to a concentration of 40-50 ng in 45 µl TE buffer, denatured by heating to 100° C. for five min, and briefly centrifuged. The denatured cDNA is prepared using the Amersham CYSCRIBE first strand cDNA labeling kit (GEH) according to the manufacturer's instructions. The labeling reaction is stopped by adding 5 µl of 0.2M EDTA, and probe is purified from unincorporated nucleotides using a GFX Purification kit (GEH). The purified probe is heated to 100° C. for five min, cooled for two min on ice, and used in membrane-based hybridizations as described below.

Probe Preparation for Slide Hybridization

Hybridization probes derived from blood mRNA are employed for screening the amplicons of Table 1 in array-based hybridizations. Probe is prepared using the Amersham CYSCRIBE Microarray Labeling kits (GEH) according to the manufacturer's instructions. Purified probe is ethanol precipitated by diluting the probe to 90 µl in DEPC-treated water, adding 2 µl of 1 mg/ml glycogen, 60 µl 5 M sodium acetate, and 300 µl 100% ethanol. The probe is centrifuged for 20 min at 20,800×g, suspended in 1211 resuspension buffer, heated to 65° C. for five min, mixed thoroughly, and stored on ice. Probe is used in slide-based hybridizations as described below.

Membrane-based Hybridization

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55° C. for two hr. The probe is diluted in 15 ml fresh hybridization solution and added to the membrane. The membrane is hybridized with the probe at 55° C. for 16 hr. Following hybridization, the membrane is washed once for 15 min at 25° C. in 1 mM Tris (pH 8.0) and 1% Sarkosyl and four times for 15 min each at 25° C. in 1 mM Tris (pH 8.0). To detect hybridization complexes, the membrane is exposed to x-ray film (Eastman Kodak) overnight at −70° C., developed, and examined visually or quantified using a scintillation counter (Beckman-Coulter, Fullerton Calif.).

Slide-based Hybridization

Probe is heated to 65° C. for five min, microcentrifuged for five min, and 1811 is pipetted onto the array surface. The array is covered with a coverslip and transferred to a waterproof chamber having a cavity just slightly larger than a microscope slide. The chamber, kept at 100% humidity internally by the addition of 140 µl of 5×SSC, is incubated for about 6.5 hr at 60° C. The arrays are washed once for 10 min at 45° C. in 1×SSC and 0.1% SDS, and three times for 10 min at 45° C. in 0.1×SSC, and dried.

Probe from one sample is hybridized to array elements, and signals are detected after hybridization complexes form. Signal strength correlates with amount of probe mRNA in the sample.

Hybridization complexes are detected with a microscope equipped with an INNOVA 70 mixed gas 10 W laser (Coherent, Santa Clara Calif.) capable of generating spectral lines at the excitation wavelength of the fluorophore with which the probe is labeled. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. Emitted light is detected by photomultiplier tube detectors (PMT R1477, Hamamatsu Photonics Systems, Bridgewater N.J.) corresponding to the two fluorophores. If more than one probe and fluorophore is used, filters positioned between the array and photomultiplier tubes separate the signals. The sensitivity of the scans is calibrated using the signal intensity generated by the control mRNAs added to the probe mix.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively by integrating the fluorescence signal to obtain a numerical value corresponding to the average intensity of the signal.

Antibody Arrays

An antibody array can be used to study proteins expressed in a sample. Monoclonal antibodies specific to the proteins, can be immobilized on a membrane, slide or dipstick or added to the wells of an ELISA plate using methods well known in the art. The array is incubated in the presence of cell lysate until protein:antibody complexes are formed. The proteins encoded by the genes or splice variants are identified by the known position of the antibody on the array. Quantification is correlated with the amount of labeling moiety in the complex and can be compared with controls and references.

Example 16

Monitoring Treatment Regimens in Patients

RT-PCR and array technologies can be used to produce and monitor or to improve patient/subject expression profiles. Once a dosage that shows an expression pattern indicative of successful treatment in a particular patient is established, any variation from that expression pattern can highlight the need for modification of the treatment regimen—administration of higher dose or different immunosuppressants to prevent transplant rejection or flare of an immune disorder. The use of blood tests (rather than biopsy in the case of heart transplant) to predict transplant rejection or the onset of an immune disorder is more sensitive and rapid than waiting for the patient to manifest allograft rejection or an acute episode of disease activity.

Expression profiles associated with successful treatment can also be used to evaluate the efficacy of alternative therapeutic regimens. Assays can be repeated on a regular basis to determine if the gene expression profile of the patient is moving toward or away from a normal reference. The results obtained from successive assays can be used to show the efficacy of treatment plan over a period ranging from several days to years.

Example 17

Viral infections Altering T-Cell Populations

When HIV infects T-cells, it causes alterations in leukocyte expression. T-cell specific splice variants of CBLB, CD8, CXCR3, FASL, ITGB7 and PDCD1 that are highly expressed in T-cells or primers or probes thereof can be used with the methods disclosed herein to monitor subjects with HIV. Early infections and HIV status can be monitored in samples obtained from the gastric mucosa, a early-stage reservoir for HIV. In addition, other indications of HIV status such as viral load, CD4 T-cell counts, opportunistic infection, response to antiretroviral therapy, progression to AIDS, rate of progression, and the occurrence of other HIV-related outcomes such as malignancy and CNS disturbance can be monitored with the methods, genes and splice variants disclosed herein.

Example 18

Splice Variant Expression in Lung Transplant Rejection

PCR was used to generate gene expression profiles for more than 300 genes in lung transplant patients with and without acute rejection. In the process of designing these assays those genes that appeared to have well documented splice variants were identified by examining the databases REFSEQ and ACEVIEW at the National Center for Biological Information at the National Library of Medicine. Two PCR assays were run. The first assay quantified all gene expression in blood using primers designed for a 3' mRNA sequence common to all splice variants of the gene. The second assay validated the expression of a particular or individual splice variant in blood using primers designed to amplify an mRNA sequence unique to the particular splice variant as described above.

RT-PCR was used with 3' and splice variant primers to quantify gene expression in two classes of blood samples. Class 1 samples were from lung transplant patients with no acute cellular rejection (NR) as documented by biopsy, and class II samples were from patients with acute cellular rejection rated as A2 (R). The genes, primer sets and amplicons encoding and associated with CD44, CD59, CORO2A, IL1R2, LAIR2, and PRDM1 proteins are set forth in Table 1 which shows the data from lung transplant subjects. Column 1 of Table 4 shows the NCBI name for the gene/protein; column 2, the p-value based on a two-tailed Student's t-test,; column 3, the fold difference of R/NR; column 4, the separation coefficient calculated as follows: separation=ave Ct (R)−ave Ct (NR)/stdev R+stdev NR where the greater the coefficient of separation, the better the performance of the 3' or splice variant probes; column 5, determination of the best probes for diagnosing or monitoring acute cellular rejection—gene versus splice variant(s); and column 6, correlation between expression of the gene and splice variant(s); column 7, average Ct based on at least two measurements recorded during PCR amplification; column 8, NCBI GI sequence identifier; column 9, the position of the first nucleotide of the amplicon generated during RT-PCR as located in the GI sequence identifier; and column 10, the position of the last nucleotide of the amplicon as located in the GI sequence identifier. The splice variant specific primers or probes of CD44v1-1N, IL1R2V4-7N, LAIR2v2-2N, and PRDM1v1-2N were superior to the 3' gene or other splice variant probes in their ability to diagnose and monitor patients with acute cellular rejection in PCR assays.

A Pearson correlation coefficient was used to compare the expression of the gene (combined expression of all splice variants) versus expression of particular or individual splice variant. Whereas average Ct values were based on at least two measurements taken during amplification, normalization is based on the expression of several genes determined to have very low variation between the two classes. Other statistical methods that can be used to establish useful correlations include Fisher exact test, Mann-Whitney test; Spearman rank correlation, and the like.

In addition, it must be noted that separation metric or p-value can be used to identify genes expressed in the same pathways or cell types, whereas genes or splice variants that are highly expressed but not highly correlated are generally active in different pathways. These genes or splice variants are very useful in that they provide non-redundant information on pathways active during immunological response and add to the sensitivity and specificity of diagnostic or screening assays.

TABLE 1

| Gene/Protein | Probe Set | GI Sequence Identifier | nt Start | End nt | Amplicon Length |
|---|---|---|---|---|---|
| ADM | 2073-5 | 4501944 | 370 | 468 | 99 |
| ADM | ADMv2-8 | 46847520 | 308 | 379 | 72 |
| CBLB | CBLB-2 | 4757919 | 2007 | 2107 | 101 |
| CBLB | CBLBv2-7 | 22921131 | 64 | 157 | 94 |
| CBLB | CBLBv3-4 | 54112419 | 2687 | 2784 | 98 |
| CXCR3 | CXCR3-7 | 4504098 | 975 | 1071 | 97 |
| CXCR3 | CXCR3v1-2 | 4504098 | 6 | 93 | 88 |
| CXCR3 | CXCR3v2-2 | 31455575 | 90 | 193 | 104 |
| CXCR4 | 269 | 56790928 | 1524 | 1622 | 99 |
| CXCR4 | CXCR4v1-4 | 51537346 | 3900 | 4035 | 136 |
| CXCR4 | CXCR4v2-2 | 56790928 | 62 | 160 | 99 |

TABLE 1-continued

| Gene/Protein | Probe Set | GI Sequence Identifier | nt Start | End nt | Amplicon Length |
|---|---|---|---|---|---|
| FASL | TNFSF6 | 4557328 | 1355 | 1467 | 113 |
| FASL | TNFSF6v2-8 | 4557328 | 506 | 599 | 94 |
| FLT3 | FLT3-3L | 4758395 | 2966 | 3086 | 121 |
| FLT3 | FLT3v1-2 | 4758395 | 2252 | 2344 | 93 |
| FLT3 | FLT3v2-2 | 23273564 | 2162 | 2289 | 128 |
| FLT3 | FLT3v3-1 | 20135745 | 61473 | 61565 | 93 |
| G6B-1 | G6B-1 | 19913372 | 250 | 353 | 104 |
| G6B-1 | G6Bv3-4 | 19913376 | 400 | 515 | 116 |
| G6B-1 | G6Bv4-2 | 19913374 | 535 | 634 | 100 |
| G6B-1 | G6Bv5-7 | 19913372 | 458 | 561 | 104 |
| G6B-1 | G6Bv6-7 | 21750976 | 1353 | 1457 | 105 |
| IL1R2 | 4685-5 | 27894332 | 47 | 143 | 97 |
| IL1R2 | IL1R2v4-7 | 27894332 | 63 | 143 | 81 |
| ITGA4 | ITGA4 | 6006032 | 4807 | 4929 | 123 |
| ITGAM | ITGAM | 6006013 | 3934 | 4022 | 89 |
| ITGAM | ITGAMv1-7 | 16553821 | 1386 | 1525 | 140 |
| ITGAM | ITGAMv2-3 | 34534634 | 439 | 535 | 97 |
| ITGAM | ITGAMv3-5 | 16553821 | 1129 | 1203 | 75 |
| ITGB7 | ITGB7 | 4504776 | 2513 | 2609 | 97 |
| ITGB7 | ITGB7v1-6 | 13551602 | 16 | 211 | 196 |
| ITGB7 | ITGB7v2-6 | 10452695 | 179 | 278 | 100 |
| ITGB7 | ITGB7v3-4 | 4504776 | 1245 | 1337 | 93 |
| MARCH8 | 2709 | 10437995 | 1845 | 1945 | 101 |
| MARCH8 | MIRv1-2 | 45433548 | 434 | 530 | 97 |
| MARCH8 | MIRv2-8 | 50539413 | 13 | 104 | 92 |
| MARCH8 | MIRv3-2 | 50539411 | 660 | 781 | 122 |
| MARCH8 | MIRv4-3 | 16552920 | 510 | 596 | 87 |
| MARCH8 | MIRv5-1 | 50539411 | 2024 | 2123 | 100 |
| PDCD1 | PDCD1 | 4826889 | 1100 | 1205 | 106 |
| PF4 | PF4 | 4505732 | 217 | 342 | 126 |
| RHOU | 6489-4 | 45827773 | 932 | 1025 | 94 |
| SEMA7A | 4647 | 4504236 | 2500 | 2595 | 96 |
| WDR40A | 873 | 7020383 | 3059 | 3134 | 76 |
| ZNFN1A1 | ZNFN1A1-3 | 31657112 | 2352 | 2449 | 98 |
| ZNFN1A1 | ZNFN1A1v1-1 | 19354733 | 370 | 471 | 102 |
| ZNFN1A1 | ZNFN1A1v2-1 | 19851931 | 103 | 199 | 97 |
| ZNFN1A1 | ZNFNIA1v3-2 | 31657112 | 745 | 842 | 98 |
| ZNFN1A1 | ZNFN1A1v5-3 | 15758908 | 575 | 674 | 100 |
| ZNFN1A1 | ZNFN1A1v6-3 | 31657112 | 196 | 295 | 100 |

TABLE 2

| Gene/Protein | Probes Sets | Average Ct | | Median Ct | | Ratio of ex | T-test | ΔT-test |
|---|---|---|---|---|---|---|---|---|
| | | R | NR | R | NR | | | |
| ADM | 2073-5 | 31.5633 | 30.8208 | 31.6675 | 30.8144 | 0.554 | 0.0036 | 1.00 |
| ADM | ADMv2-8 | 34.4696 | 33.7143 | 34.5830 | 33.7004 | 0.542 | 0.0041 | 1.00 |
| CBLB | CBLB-2 | 29.3887 | 29.6322 | 29.3944 | 29.5915 | 1.146 | 0.0414 | 1.00 |
| CBLB | CBLBv3-4 | 29.8052 | 29.9422 | 29.8058 | 29.9936 | 1.139 | 0.2469 | 0.17 |
| CBLB | CBLBv2-7 | 30.2565 | 30.3962 | 30.2274 | 30.2818 | 1.038 | 0.5152 | 0.08 |
| CXCR3 | CXCR3-7 | 30.2030 | 30.6934 | 30.2142 | 30.5862 | 1.294 | 0.0113 | 1.00 |
| CXCR3 | CXCR3v1-2 | 30.0739 | 30.6095 | 30.0772 | 30.4076 | 1.257 | 0.0057 | 7.27 |
| CXCR3 | CXCR3v2-2 | 32.8293 | 33.2941 | 32.8390 | 33.0298 | 1.141 | 0.0215 | 0.53 |
| CXCR4 | 269 | 26.3184 | 25.7596 | 26.5589 | 25.6575 | 0.535 | 0.0031 | 1.00 |
| CXCR4 | CXCR4v1-4 | 30.9280 | 30.5804 | 30.8749 | 30.4323 | 0.736 | 0.1490 | 0.02 |
| CXCR4 | CXCR4v2-2 | 26.0147 | 25.3536 | 26.1892 | 25.3275 | 0.550 | 0.0002 | 45.72 |
| FASL | TNFSF6 | 32.7363 | 33.4230 | 32.7707 | 33.3424 | 1.486 | 0.0134 | 1.00 |
| FASL | TNFSF6v2-8 | 31.1668 | 31.7190 | 31.0748 | 31.6529 | 1.493 | 0.0498 | 0.27 |
| FLT3 | FLT3-3L | 32.0645 | 31.3091 | 32.5544 | 31.3473 | 0.433 | 0.0230 | 1.00 |
| FLT3 | FLT3v1-2 | 32.0629 | 31.5519 | 32.3861 | 31.4972 | 0.540 | 0.0621 | 0.37 |
| FLT3 | FLT3v2-2 | 31.7731 | 31.2751 | 32.0391 | 31.4331 | 0.657 | 0.0386 | 0.60 |
| FLT3 | FLT3v3-1 | 34.7475 | 33.7883 | 35.0354 | 33.5924 | 0.368 | 0.0060 | 3.82 |
| G6B-1 | G6B-1 | 26.6644 | 26.2038 | 26.5108 | 26.4872 | 0.984 | 0.1107 | 1.00 |
| G6B-1 | G6Bv5-7 | 27.0779 | 26.6530 | 26.9373 | 26.9823 | 1.032 | 0.1451 | 0.76 |
| G6B-1 | G6Bv6-7 | 26.4196 | 26.0085 | 26.4362 | 26.1674 | 0.830 | 0.1817 | 0.61 |
| G6B-1 | G6Bv4-2 | 27.7968 | 27.4253 | 27.7040 | 27.7501 | 1.033 | 0.2032 | 0.54 |
| G6B-1 | G6Bv3-4 | 34.2815 | 34.1681 | 34.3203 | 34.3681 | 1.034 | 0.6748 | 0.16 |
| IL1R2 | 4685-5 | 34.3785 | 33.6843 | 34.5634 | 33.8557 | 0.612 | 0.0409 | 1.00 |
| IL1R2 | IL1R2v4-7 | 32.9952 | 32.2761 | 33.3391 | 32.1796 | 0.448 | 0.0249 | 1.64 |
| ITGA4 | ITGA4 | 27.8660 | 28.1908 | 27.8027 | 28.1324 | 1.257 | 0.0041 | 1.00 |
| ITGAM | ITGAM | 26.7722 | 26.5933 | 26.6746 | 26.6148 | 0.959 | 0.0926 | 1.00 |
| ITGAM | ITGAMv1-7 | 31.6609 | 31.7693 | 31.5905 | 31.8286 | 1.179 | 0.4961 | 0.00 |

TABLE 2-continued

| Gene/Protein | Probes Sets | Average Ct R | Average Ct NR | Median Ct R | Median Ct NR | Ratio of ex | T-test | ΔT-test |
|---|---|---|---|---|---|---|---|---|
| ITGAM | ITGAMv2-3 | 32.0526 | 31.9603 | 32.0532 | 31.9339 | 0.921 | 0.4848 | 0.00 |
| ITGAM | ITGAMv3-5 | 29.8250 | 29.7096 | 29.6649 | 29.5841 | 0.946 | 0.5014 | 0.00 |
| ITGB7 | ITGB7 | 27.7926 | 28.0682 | 27.8002 | 28.0174 | 1.162 | 0.0307 | 1.00 |
| ITGB7 | ITGB7v1-6 | 32.7108 | 33.1991 | 32.6486 | 33.3140 | 1.586 | 0.0023 | 13.50 |
| ITGB7 | ITGB7v2-6 | 31.6821 | 31.8997 | 31.5861 | 31.7069 | 1.087 | 0.1629 | 0.19 |
| ITGB7 | ITGB7v3-4 | 28.1615 | 28.3519 | 28.2294 | 28.3607 | 1.095 | 0.1196 | 0.26 |
| MARCH8 | 2709 | 29.3303 | 29.5345 | 29.5540 | 29.5569 | 1.002 | 0.2257 | 1.00 |
| MARCH8 | MIRv1-2 | 28.5654 | 28.7999 | 28.7751 | 28.8784 | 1.074 | 0.1257 | 1.80 |
| MARCH8 | MIRv2-8 | 34.5638 | 34.8143 | 34.5646 | 34.6522 | 1.063 | 0.2914 | 0.77 |
| MARCH8 | MIRv3-2 | 30.1286 | 30.3746 | 30.2330 | 30.3265 | 1.067 | 0.0702 | 3.22 |
| MARCH8 | MIRv4-3 | 30.8578 | 30.8974 | 31.1050 | 31.0466 | 0.960 | 0.8672 | 0.26 |
| MARCH8 | MIRv5-1 | 28.2706 | 28.5473 | 28.5125 | 28.5298 | 1.012 | 0.0978 | 2.31 |
| PDCD1 | PDCD1 | 32.0936 | 32.5487 | 32.1405 | 32.6298 | 1.404 | 0.0355 | 1.00 |
| PF4 | PF4 | 25.1649 | 24.6590 | 25.2115 | 24.6835 | 0.694 | 0.0220 | 1.00 |
| RHOU | 6489-4 | 29.9122 | 30.1781 | 29.9526 | 30.1519 | 1.148 | 0.0100 | 1.00 |
| SEMA7A | 4647 | 34.2925 | 34.6421 | 34.2949 | 34.6740 | 1.301 | 0.0219 | 1.00 |
| WDR40A | 873 | 28.2350 | 28.6684 | 28.5440 | 28.7566 | 1.159 | 0.0189 | 1.00 |
| ZNFN1A1 | ZNFN1A1-3 | 26.7023 | 26.8095 | 26.7176 | 26.7714 | 1.038 | 0.1248 | 1.00 |
| ZNFN1A1 | ZNFN1A1v1-1 | 30.9573 | 31.1228 | 30.9865 | 31.1640 | 1.131 | 0.0962 | 1.30 |
| ZNFN1A1 | ZNFN1A1v2-1 | 29.3316 | 29.1978 | 29.3258 | 29.2446 | 0.945 | 0.1036 | 1.20 |
| ZNFN1A1 | ZNFN1A1v3-2 | 27.3914 | 27.4549 | 27.3878 | 27.4618 | 1.053 | 0.3521 | 0.35 |
| ZNFN1A1 | ZNFN1A1v5-3 | 29.1596 | 29.3809 | 29.1773 | 29.3440 | 1.123 | 0.0359 | 3.47 |
| ZNFN1A1 | ZNFN1A1v6-3 | 26.5807 | 26.5295 | 26.5105 | 26.5631 | 1.037 | 0.5542 | 0.23 |

TABLE 3

| Gene/Protein | Probe Sets | B-cells | Granulocytes | Monocytes | T-cells | Other | Comparative Expression and Comments |
|---|---|---|---|---|---|---|---|
| ADM | 2073-5 | | | low | | | |
| ADM | ADMv2-8 | | | | | | Expression < 2073-5 with similar distribution. |
| CBLB | CBLB-2 | low | low | low | high | | |
| CBLB | CBLBv3-4 | | | | | | Expression ≃ CBLB-2 with similar distribution |
| CBLB | CBLBv2-7 | | | | | | Expression ≃ CBLB-2 with similar distribution |
| CXCR3 | CXCR3-7 | low | high | | high | | |
| CXCR3 | CXCR3v1-2 | | | | | | Expression ≧ CXCR3-7 with similar distribution |
| CXCR3 | CXCR3v2-2 | | | | | | Expression < CXCR3-7 with similar distribution |
| CXCR4 | 269 | highest | moderate | moderate | moderate | | |
| CXCR4 | CXCR4v1-4 | | | | | | Expression < 269 |
| CXCR4 | CXCR4v2-2 | | | | | | Expression ≧ 269 |
| FASL | TNFSF6 | | | | only | | |
| FASL | TNFSF6v2-8 | | | | | | Expression > TNFsf6 variant |
| FLT3 | FLT3-3L | | low | low | | | |
| FLT3 | FLT3v1-2 | | | | | | Expression ~ FLT3-3L with similar distribution |
| FLT3 | FLT3v2-2 | | | | | | Expression ≃ FLT3-3L with similar distribution |
| FLT3 | FLT3v3-1 | | | | | | Expression < FLT3-3L with similar distribution |
| G6B-1 | G6B-1 | | | very low | | Platelets* | Expression highest in platelets |
| G6B-1 | G6Bv3-4 | | | | | Platelets* | Expression highest in platelets, but lowest of G6B-1 |
| G6B-1 | G6Bv4-2 | | | | | Platelets* | Expression highest in platelets |
| G6B-1 | G6Bv5-7 | | | | | Platelets* | Expression highest in platelets |
| G6B-1 | G6Bv6-7 | | | | | Platelets* | Expression highest in platelets |
| IL1R2 | 4685-5 | | | low | | | |
| IL1R2 | IL1R2v4-7 | | | | | | Expression > 4685-5 with a similar distribution |
| ITGA4 | ITGA4 | detected | detected | highest | detected | | |
| ITGAM | ITGAM | detected | detected | highest | detected | | |
| ITGAM | ITGAMv1-7 | | | | | | Expression < ITGAM with similar distribution |
| ITGAM | ITGAMv2-3 | | | | | | Expression < ITGAM with similar distribution |
| ITGAM | ITGAMv3-5 | | | | | | Expression < ITGAM with similar distribution |
| ITGB7 | ITGB7 | detected | detected | detected | highest | | |
| ITGB7 | ITGB7v1-6 | | | | | | Expression < IITGB7 with similar distribution |
| ITGB7 | ITGB7v2-6 | | | | | | Expression < ITGB7 with similar distribution |
| ITGB7 | ITGB7v3-4 | | | | | | Expression ~ ITGB7 with similar distribution |
| MARCH8 | 2709 | low | low | low | low | Erythrocytes* | *Expression highest in erythrocytes |
| MARCH8 | MIRv1-2 | | | | | | Expression ≃ 2709 with similar distribution |
| MARCH8 | MIRv2-8 | | | | | | Expression < 2709 but not detected in erythrocytes |
| MARCH8 | MIRv3-2 | | | | | | Expression ≃ 2709 with similar distribution |
| MARCH8 | MIRv4-3 | | | | | | Expression < 2709 with a similar distribution |
| MARCH8 | MIRv5-1 | | | | | | Expression > 2709 with similar distribution |
| PDCD1 | PDCD1 | | | | only | | |
| PF4 | PF4 | | | | low | Platelets* | *Expression highest in platelets |
| RHOU | 6489-4 | detected | detected | detected* | detected | | *Expression highest in monocytes |
| SEMA7A | 4647 | low | low | | low | | |
| WDR40A | 873 | detected | detected | detected | detected | Erythrocytes* | *Expression highest in erythrocytes |
| ZNFN1A1 | ZNFN1A1-3 | detected | detected | detected | detected | | |

TABLE 3-continued

| Gene/Protein | Probe Sets | B-cells | Granulocytes | Monocytes | T-cells | Other | Comparative Expression and Comments |
|---|---|---|---|---|---|---|---|
| ZNFN1A1 | ZNFN1A1v1-1 | | | | | | Expression < ZNFN1A1-3 with a similar distribution |
| ZNFN1A1 | ZNFN1A1v2-1 | | | | | | Expression < ZNFN1A1-3 with a similar distribution |
| ZNFN1A1 | ZNFN1A1v3-2 | | | | | | Expression ≃ ZNFN1A1-3 with a similar distribution |
| ZNFN1A1 | ZNFN1A1v5-3 | | | | | | Expression < ZNFN1A1-3 with a similar distribution |
| ZNFN1A1 | ZNFN1A1v6-3 | | | | | | Expression ≃ ZNFN1A1-3 with a similar distribution |

TABLE 4

| Gene | T-test p value | Coefficient of Fold R/NR Separation | Best Probes for Detection of ACR | Pearson Correlation coefficient of Gene to SV | Average Ct during PCR | GI Sequence Identifier | nt Start | End nt |
|---|---|---|---|---|---|---|---|---|
| CD59 | 0.0080 | 0.70 0.30 | Gene | | 35.3 | 42761473 | 7103 | 7194 |
| CD59v2 | 0.0628 | 0.84 0.21 | | 0.64 | 29.9 | 42716300 | 89 | 224 |
| CORO2A | 0.0062 | 0.76 0.30 | Gene | | 31.7 | 16554582 | 1433 | 1528 |
| CORO2Av2 | 0.0336 | 0.83 0.23 | | 0.92 | 31.7 | 34335234 | 66 | 144 |
| PRDM1 | 0.0325 | 1.26 0.25 | | | 27.6 | 33946272 | 2761 | 2838 |
| PRDM1v1 | 0.0105 | 1.28 0.29 | Splice Variant | 0.73 | 31.9 | 33946272 | 336 | 433 |
| CD44 | 0.2765 | 1.05 0.12 | | | 25.2 | 48255940 | 1290 | 1378 |
| CD44v1 | 0.0365 | 1.51 0.24 | Splice Variant | 0.16 | 33 | 48255936 | 1540 | 1641 |
| CD44v2 | 0.0737 | 1.24 0.20 | Splice Variant | 0.67 | 32.8 | 48255938 | | |
| IL1R2 | 0.7083 | 0.88 0.04 | | | 34.2 | 27894332 | 972 | 1116 |
| IL1R2V4 | 0.4592 | 0.81 0.08 | Splice Variant | 0.94 | 34.5 | 27894332 | 63 | 143 |
| LAIR2 | 0.1528 | 1.54 0.19 | | | 34 | 32481203 | 403 | 477 |
| LAIR2v2 | 0.0027 | 1.96 0.36 | Splice Variant | 0.05 | 34.7 | 32481204 | 403 | 499 |

What is claimed is:

1. A method for diagnosing or monitoring the status of a transplant comprising:
   (a) selecting a splice variant of a gene, wherein the splice variant comprises a sequence identified by a National Center for Biotechnology Information (NCBI) GI Number selected from the group consisting of 4504098, 56790928, 20135745, 27894332, 13551602, 50539411, 15758908, 33946272, 48255936, and 32481204;
   (b) detecting expression of the splice variant in a sample using a probe that specifically detects the expression of the splice variant; and
   (c) diagnosing or monitoring the status of the transplant based on the expression of the splice variant in the sample.

2. The method of claim 1, wherein the transplant is an allograft selected from the group consisting of an artificial organ, a mechanical organ, bone marrow, a cornea, a heart, a kidney, a liver, a lung, an organ-system, a pancreas, pancreatic islet cells, stem cells, skin tissue, skin cells, and a xenotransplant.

3. The method of claim 1, wherein the transplant is a heart allograft.

4. The method of claim 1, wherein diagnosing or monitoring the status of a transplant comprises diagnosing or monitoring acute cellular rejection.

* * * * *